(12) United States Patent
Stanton et al.

(10) Patent No.: US 12,053,586 B2
(45) Date of Patent: Aug. 6, 2024

(54) MEDICAL TUBES FOR BREATHING CIRCUIT

(71) Applicant: Fisher & Paykel Healthcare Limited, Auckland (NZ)

(72) Inventors: James William Stanton, Auckland (NZ); Gavin Walsh Millar, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 457 days.

(21) Appl. No.: 16/317,920

(22) PCT Filed: Jul. 21, 2017

(86) PCT No.: PCT/NZ2017/050099
§ 371 (c)(1),
(2) Date: Jan. 15, 2019

(87) PCT Pub. No.: WO2018/016975
PCT Pub. Date: Jan. 25, 2018

(65) Prior Publication Data
US 2021/0252248 A1 Aug. 19, 2021

Related U.S. Application Data

(60) Provisional application No. 62/365,285, filed on Jul. 21, 2016.

(51) Int. Cl.
*A61M 16/10* (2006.01)
*A61M 16/06* (2006.01)
(Continued)

(52) U.S. Cl.
CPC .......... *A61M 16/109* (2014.02); *A61M 16/06* (2013.01); *A61M 16/0875* (2013.01);
(Continued)

(58) Field of Classification Search
CPC .. A61M 16/00; A61M 16/08; A61M 16/0875; A61M 16/0883; A61M 16/109;
(Continued)

(56) References Cited

U.S. PATENT DOCUMENTS

| 2,898,941 A | 8/1959 | Kilcup |
| 3,307,542 A | 3/1967 | Andreasen |

(Continued)

FOREIGN PATENT DOCUMENTS

| AU | 2006320626 | 6/2007 |
| CN | 104955510 | 9/2015 |

(Continued)

OTHER PUBLICATIONS

International Preliminary Report on Patentability, PCT/NZ2017/050099, dated Jan. 22, 2019, 15 pages.
(Continued)

*Primary Examiner* — Joseph D. Boecker
(74) *Attorney, Agent, or Firm* — Knobbe Martens Olson & Bear LLP

(57) ABSTRACT

A breathing circuit for use in respiratory therapy includes an inspiratory tube and an expiratory tube. The inspiratory tube of the breathing circuit has a smooth bore. The expiratory tube of the breathing circuit is corrugated. Preferably, the expiratory tube is vapor permeable. Using the combination of a smooth bore inspiratory tube with a corrugated expiratory tube has the unexpected result of improving the performance of the breathing circuit and its components.

23 Claims, 13 Drawing Sheets

(51) Int. Cl.
*A61M 16/08* (2006.01)
*A61M 16/16* (2006.01)
(52) U.S. Cl.
CPC . *A61M 16/1095* (2014.02); *A61M 2205/3331* (2013.01); *A61M 2205/3368* (2013.01)
(58) Field of Classification Search
CPC ............. A61M 16/1095; A61M 16/16; A61M 2205/3368
See application file for complete search history.

(56) References Cited

U.S. PATENT DOCUMENTS

| | | | |
|---|---|---|---|
| 3,858,615 | A | 1/1975 | Weigl |
| 3,865,106 | A | 2/1975 | Palush |
| 4,007,737 | A | 2/1977 | Paluch |
| 4,265,235 | A | 5/1981 | Fukunaga |
| 4,463,755 | A | 8/1984 | Suzuki |
| 4,967,744 | A | 11/1990 | Chua |
| 5,357,948 | A | 10/1994 | Eilentropp |
| 5,404,873 | A | 4/1995 | Leagre et al. |
| 5,501,212 | A | 3/1996 | Psaros |
| 5,735,266 | A | 4/1998 | Smith |
| 5,778,872 | A | 7/1998 | Fukunaga et al. |
| 5,937,856 | A | 8/1999 | Jonasson et al. |
| 6,078,730 | A | 6/2000 | Huddart et al. |
| 6,167,883 | B1 | 1/2001 | Beran et al. |
| 6,209,539 | B1 | 4/2001 | Loescher et al. |
| 6,398,197 | B1 | 6/2002 | Dickinson et al. |
| 6,523,538 | B1 | 2/2003 | Wikefeldt |
| 6,536,428 | B1 | 3/2003 | Smith et al. |
| 6,595,203 | B1 | 7/2003 | Bird |
| 6,598,604 | B1 | 7/2003 | Seakins |
| 8,360,059 | B2 | 1/2013 | Koulechov et al. |
| 8,402,970 | B2 | 3/2013 | Levi et al. |
| 8,944,056 | B2 | 3/2015 | Virr et al. |
| 9,108,227 | B2 | 8/2015 | Frater |
| 9,182,062 | B2 | 11/2015 | Kwok et al. |
| 2001/0054422 | A1 | 12/2001 | Smith et al. |
| 2002/0002976 | A1 | 1/2002 | Smith et al. |
| 2002/0078733 | A1 | 6/2002 | Seakins et al. |
| 2002/0100320 | A1 | 8/2002 | Smith et al. |
| 2002/0124847 | A1 | 9/2002 | Smith et al. |
| 2003/0075176 | A1 | 4/2003 | Fukunaga et al. |
| 2003/0111249 | A1 | 6/2003 | Edirisuriya et al. |
| 2003/0154977 | A1 | 8/2003 | White et al. |
| 2003/0188746 | A1 | 10/2003 | Daugherty |
| 2003/0230306 | A1 | 12/2003 | Castor et al. |
| 2004/0079371 | A1 | 4/2004 | Gray |
| 2004/0081784 | A1 | 4/2004 | Smith et al. |
| 2005/0150505 | A1 | 7/2005 | Burrow et al. |
| 2005/0152733 | A1 | 7/2005 | Patel |
| 2007/0125379 | A1 | 6/2007 | Pierro et al. |
| 2008/0251082 | A1 | 10/2008 | Sinha |
| 2008/0276938 | A1 | 11/2008 | Jeppesen |
| 2010/0132706 | A1 | 6/2010 | Nashed |
| 2010/0224195 | A1 | 9/2010 | Henry |
| 2011/0108031 | A1 | 5/2011 | Korneff et al. |
| 2012/0125332 | A1 | 5/2012 | Niland et al. |
| 2012/0125333 | A1 | 5/2012 | Bedford et al. |
| 2012/0152247 | A1 | 6/2012 | Labollita |
| 2012/0266888 | A1 | 10/2012 | Dwyer et al. |
| 2013/0098360 | A1* | 4/2013 | Hurmez ............ A61M 16/0057 128/203.12 |
| 2014/0158128 | A1 | 6/2014 | Heimel |
| 2014/0202462 | A1* | 7/2014 | Stoks ................ A61M 16/0883 128/204.18 |
| 2014/0283829 | A1 | 9/2014 | Miller |
| 2014/0283834 | A1 | 9/2014 | Ahmad et al. |
| 2014/0318535 | A1 | 10/2014 | Bullock et al. |
| 2014/0338666 | A1 | 11/2014 | Visveshwara et al. |
| 2015/0101597 | A1 | 4/2015 | Boucher et al. |
| 2015/0108670 | A1 | 4/2015 | Magee |
| 2015/0306333 | A1* | 10/2015 | Amadio ................ A61M 39/08 128/204.17 |
| 2015/0352308 | A1 | 12/2015 | Cullen et al. |
| 2016/0022949 | A1* | 1/2016 | Milne ............... A61M 16/0875 128/201.13 |
| 2016/0030698 | A1 | 2/2016 | Kolk et al. |
| 2016/0303342 | A1* | 10/2016 | Dwyer .................. A61M 16/16 |
| 2017/0072156 | A1 | 3/2017 | Nashed |
| 2018/0104436 | A1 | 4/2018 | Leonard et al. |
| 2018/0311459 | A1 | 11/2018 | Winkler et al. |
| 2021/0046272 | A1 | 2/2021 | Buswell et al. |
| 2021/0252248 | A1 | 8/2021 | Stanton et al. |

FOREIGN PATENT DOCUMENTS

| | | | |
|---|---|---|---|
| CN | 105339032 | 2/2016 | |
| CN | 105343971 | 2/2016 | |
| EP | 0579384 | 1/1994 | |
| EP | 0621050 | 10/1994 | |
| EP | 1075849 | 5/2005 | |
| EP | 1621224 | 2/2006 | |
| JP | 2013-514849 | 5/2013 | |
| JP | 2016-055120 | 4/2016 | |
| WO | WO 2003/022342 | 3/2003 | |
| WO | WO 2004/024429 | 3/2004 | |
| WO | WO 2004/105848 | 12/2004 | |
| WO | WO 2006/019323 | 2/2006 | |
| WO | WO 2011/077250 | 6/2011 | |
| WO | WO 2011/149362 | 12/2011 | |
| WO | WO 2011/162622 | 12/2011 | |
| WO | WO 2012/033421 | 3/2012 | |
| WO | WO 2012/164407 | 12/2012 | |
| WO | WO 2013/055235 | 4/2013 | |
| WO | WO 2013/137753 | 9/2013 | |
| WO | WO 2013/147623 | 10/2013 | |
| WO | WO 2013/162386 | 10/2013 | |
| WO | WO 2014/003579 | 1/2014 | |
| WO | WO 2014/077706 | 5/2014 | |
| WO | WO 2014/088430 | 6/2014 | |
| WO | WO-2014088430 A1 * | 6/2014 | ........ A61M 16/0875 |
| WO | WO 2014/129911 | 8/2014 | |
| WO | WO 2014/142677 | 9/2014 | |
| WO | WO 2014/142679 | 9/2014 | |
| WO | WO 2014/142682 | 9/2014 | |
| WO | WO 2015/038013 | 3/2015 | |
| WO | WO 2015/038014 | 3/2015 | |
| WO | WO 2015/174859 | 11/2015 | |
| WO | WO 2016/048172 | 3/2016 | |
| WO | WO 2016/080847 | 5/2016 | |
| WO | WO 2016/085354 | 6/2016 | |
| WO | WO 2018/217105 | 8/2018 | |
| WO | WO 2019/147142 | 8/2019 | |

OTHER PUBLICATIONS

International Search Report, PCT/NZ2017/050099, dated Oct. 18, 2017, 10 pages.

* cited by examiner

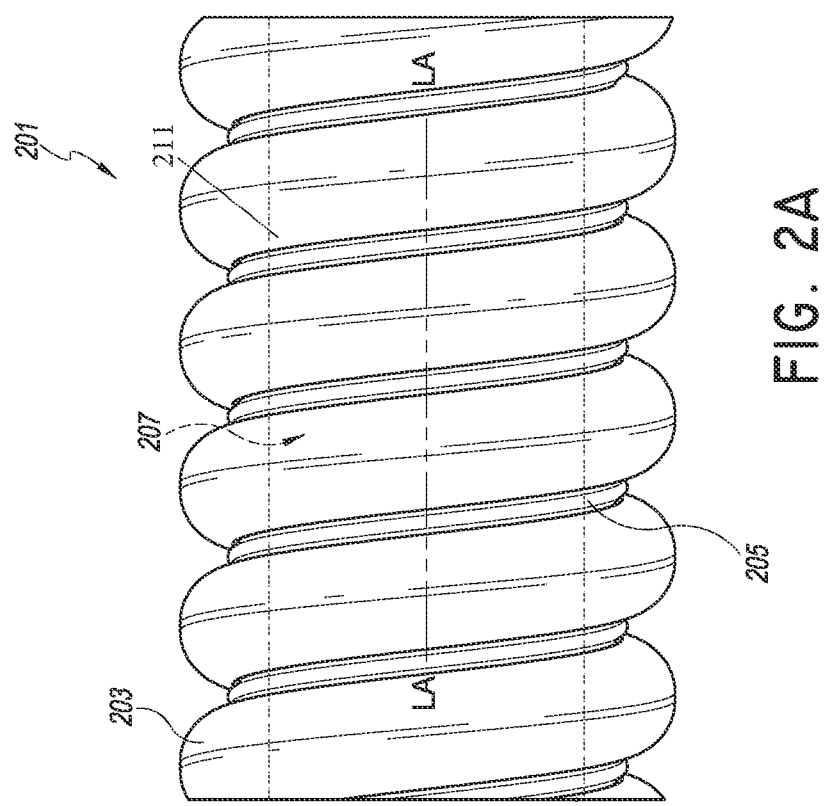

MEDICAL TUBES FOR BREATHING CIRCUIT

INCORPORATION BY REFERENCE

This application claims priority from U.S. provisional patent application 62/365,285 filed 21 Jul. 2016, the entire contents of which is hereby incorporated by reference in its entirety. In addition, the disclosure below references various features of U.S. patent application Ser. No. 13/517,925, published as U.S. Patent Application Publication No. 2013/0098360 A1, U.S. patent application Ser. No. 14/123,485, published as U.S. Patent Application Publication No. 2014/0202462 A1, and U.S. patent application Ser. No. 14/649,801, published as U.S. Patent Application Publication No. 2015/0306333 A1. The entire disclosures of those applications and publications are hereby made part of this specification as if set forth fully herein and incorporated by reference for all purposes, for all that they contain.

BACKGROUND

Field of the Invention

This disclosure relates generally to tubes suitable for medical use, and in particular to medical tubes for use in breathing circuits suitable for providing humidified gases to a patient and/or removing gases from a patient, such as in respiratory humidification systems.

Description of the Related Art

In breathing circuits, various components transport warm and/or humidified gases to and from patients. Respiratory humidification helps reduce the likelihood of infection and/or tissue damage.

SUMMARY

Certain features, aspects, and advantages of the present disclosure recognize a need for improvements that can increase the removal of vapor from expiratory gases in an expiratory tube while increasing the amount of vapor in humidified gases delivered to a patient through an inspiratory tube without increasing the overall resistance to flow in the tubes. Certain features, aspects, and advantages of the present disclosure recognize a need for improvements that reduce the compressible volume of a breathing circuit, or at least reduce the compressible volume of a limb of a breathing circuit. As described herein, there can be a tradeoff with both the compressible volume and resistance to flow between the inspiratory tube and the expiratory tube. There can be a reduction of compressible volume and/or resistance to flow in the inspiratory tube and an increase of compressible volume and/or resistance to flow in the expiratory tube. The reduction of compressible volume in the inspiratory tube can, at least in part, be due to a reduction in the inspiratory tube diameter. The reduction in tube diameter may be allowed by a reduction in resistance to flow which can, at least in part, be due to having a smooth bore. The increase of compressible volume in the expiratory tube can, at least in part, be due to increased surface area of the wall, diameter of the tube, cross-sectional area of the tube, or length of the walls of the expiratory tube. The increase of resistance to flow in the expiratory tube can be due, at least in part, to corrugations. The increased compressible volume and increased resistance to flow in the expiratory tube can improve its permeability due to various factors as described herein. This tradeoff between the inspiratory tube and expiratory tube can maintain the same overall compressible volume and/or resistance to flow in the breathing circuit as a whole.

The lower the compressible volume of a breathing circuit, the lower the pneumatic compliance of the breathing circuit for a fixed extensibility, and the lower the pneumatic compliance of a breathing circuit relative to the patient lung compliance, the less potential there is for error in delivered tidal volume.

A breathing circuit can include an inspiratory limb for carrying inspiratory gases to a patient. The inspiratory limb can include a first elongate member comprising a hollow body spirally wound to form at least in part a first elongate tube having a longitudinal axis, a first lumen extending along the longitudinal axis, and a hollow wall surrounding the lumen. The inspiratory limb can include a second elongate member spirally wound and joined between adjacent turns of the first elongate member, the second elongate member forming at least a portion of the lumen of the first elongate tube. The breathing circuit can include an expiratory limb for carrying exhaled gases from the patient. The expiratory limb can include an inlet and an outlet. The expiratory limb can include a third elongate member comprising a second tube enclosing a second lumen. The second lumen can be configured to contain a bulk flow of the exhaled gases and the second tube is permeable to water vapor and substantially impermeable to liquid water and bulk flow of the exhaled gases.

The wall of the expiratory tube can comprise a foamed polymer that is permeable to water vapor and substantially impermeable to liquid water and bulk flow of the exhaled gases. The foamed polymer can comprise a solid thermoplastic elastomer material having cell voids distributed throughout. The first lumen of the inspiratory limb can have a smooth bore. The second elongate member of the inspiratory limb can enclose at least one heating element. The first elongate member of the inspiratory limb can form in longitudinal cross-section a plurality of bubbles with a flattened surface at the lumen. The second elongate member of the inspiratory limb can enclose at least one heating element, and wherein the at least one inspiratory heating element is between a bubble of the plurality of bubbles and the inspiratory central bore. The third elongate member of the expiratory limb can be corrugated. The first elongate tube can enclose a heating element within its lumen. The third elongate member of the expiratory limb can enclose a heating element within the second lumen. The third elongate member of the expiratory limb can comprise a heating element attached to the inner wall of the second tube. The third elongate member of the expiratory limb can comprise a heating element embedded in the wall of the second tube. The second tube can have an inner surface adjacent to the second lumen and the expiratory limb further comprises a plurality of reinforcing ribs circumferentially arranged around the inner surface and generally longitudinally aligned between the inlet and the outlet.

A device can include a breathing circuit. The breathing circuit can include an inspiratory tube configured to receive the inspiratory gases flow from a gas source, the inspiratory tube comprising an inspiratory inlet, an inspiratory outlet, and a wall enclosing an inspiratory central bore. The inner wall of the inspiratory tube can be smooth. The breathing circuit can include an expiratory tube configured to receive an expiratory gases flow from a patient. The expiratory tube can include an expiratory inlet, an expiratory outlet, and a wall enclosing an expiratory central bore. The inner wall of the expiratory tube can be corrugated. The wall of the expiratory tube can be permeable to water vapor and substantially impermeable to liquid and bulk flow of the exhaled gases flowing therethrough.

The wall of the expiratory tube can comprise a foamed polymer that is permeable to water vapor and substantially impermeable to liquid water and bulk flow of the exhaled gases. The inspiratory tube can enclose a heating element within its central bore. The inspiratory tube can comprise a heating element attached to its wall. The inspiratory tube can comprise a heating element embedded in its wall. The expiratory tube can comprise a heating element within its central bore. The expiratory tube can comprise a heating element attached to its inner wall. The expiratory tube can comprise a heating embedded within its inner wall. The inspiratory tube can comprise in longitudinal cross-section a plurality of bubbles with a flattened surface at the lumen. The inspiratory tube can comprise at least one heating element, wherein the at least one inspiratory heating element is between a bubble of the plurality of bubbles and the inspiratory central bore. The expiratory tube can comprise a plurality of reinforcing ribs circumferentially arranged around the inner surface and generally longitudinally aligned between the inlet and the outlet. The breathing circuit can include a humidifier configured to humidify inspiratory gases flow to a patient. The humidifier can include a humidification chamber configured to store a volume of liquid and configured to be in fluid communication with the inspiratory gases flow. The humidifier can include a heater configured to heat the volume of liquid in the humidification chamber to create vapor, such that the inspiratory gases flow is humidified by the vapor.

A respiratory apparatus can include a humidifier configured to humidify an inspiratory gases flow to a patient. The respiratory apparatus can include an inspiratory tube configured to receive the inspiratory gases flow from the humidifier. The inspiratory tube can include an inspiratory inlet, an inspiratory outlet, and a wall enclosing an inspiratory central bore. The inner wall of the inspiratory tube can be smooth. The respiratory apparatus can include an expiratory tube configured to receive an expiratory gases flow from the patient. The expiratory tube can include an expiratory inlet, an expiratory outlet, and a wall enclosing an expiratory central bore. The expiratory central bore can be corrugated. The wall of the expiratory tube can be permeable to water vapor and substantially impermeable to liquid and bulk flow of the exhaled gases flowing therethrough.

The inspiratory tube can comprise at least one heating element within its central bore. The inspiratory tube can comprise at least one heating element attached to its inner wall. The inspiratory tube can comprise at least one heating element enclosed within its wall. The expiratory tube can comprise at least one heating element within the expiratory central bore. The expiratory tube can comprise at least one heating element attached to its inner wall. The expiratory tube can comprise at least one heating element embedded within its inner wall. The inspiratory tube can comprise a spirally wound member that forms in longitudinal cross-section a plurality of bubbles with a flattened surface at the inspiratory central bore. The inspiratory tube can enclose at least one heating element, and the at least one inspiratory heating element can be between a bubble of the plurality of bubbles and the inspiratory central bore. The wall of the expiratory tube can comprise a foamed polymer.

A respiratory apparatus can include a humidifier configured to humidify an inspiratory gases flow to a patient. The humidifier can include a humidification chamber configured to store a volume of liquid and configured to be fluid communication with the inspiratory gases flow. The humidifier can include a heater configured to heat the volume of liquid in the humidification chamber to create vapor, such that the inspiratory gases flow is humidified by the vapor. The respiratory apparatus can include an inspiratory tube configured to receive the humidified inspiratory gases flow from the humidifier. The inspiratory tube can include a wall enclosing an inspiratory central bore. The inspiratory central bore of the inspiratory tube can be smooth. The inspiratory tube can include a spirally wound first elongate member that forms in longitudinal cross-section a plurality of bubbles with a flattened surface at the inspiratory central bore. The bubbles can be configured to insulate the inspiratory central bore. The inspiratory tube can include a spirally wound second elongate member joined between adjacent turns of the first elongate member, the second elongate member forming at least a portion of the lumen of the first elongate tube and comprising at least one inspiratory heating element embedded within the second elongate member. The respiratory apparatus can include an expiratory tube configured to receive an expiratory gases flow from the patient. The expiratory tube can include a conduit enclosing an expiratory central bore. The expiratory central bore can be corrugated. The conduit can be permeable to water vapor and substantially impermeable to liquid flow therethrough. The expiratory tube can include at least one expiratory heating element within the expiratory central bore. The respiratory apparatus can include a control system configured to deliver power to the heater of the humidifier, the at least one inspiratory heating element, and the at least one expiratory heating element.

The wall of the expiratory tube can comprise a foamed polymer that is permeable to water vapor and substantially impermeable to liquid water and bulk flow of the exhaled gases. The foamed polymer can comprise a solid thermoplastic elastomer material having cell voids distributed throughout. The at least one inspiratory heating element can be between a bubble of the plurality of bubbles and the inspiratory central bore. The respiratory apparatus can include a patient interface assembly between the inspiratory tube and the expiratory tube. The power delivered by the control system can be calculated to provide increased humidification by the humidifier and controlled condensate management by the at least one expiratory heating element and the at least one inspiratory heating element. The respiratory apparatus can include a ventilator configured to provide the inspiratory gases flow and receive the expiratory gases flow. The ventilator can be configured to provide a pulsatile inspiratory gases flow to the humidifier. The ventilator can be configured to provide a constant inspiratory gases flow to the humidifier. The ventilator can be configured to provide a bias flow of gases.

A respiratory apparatus can include a humidifier configured to humidify an inspiratory gases flow to a patient. The respiratory apparatus can include an inspiratory tube configured to receive the inspiratory gases flow from a gas source. The inspiratory tube can include an inspiratory inlet, an inspiratory outlet, and a wall enclosing an inspiratory central bore. The inner wall of the inspiratory tube can be smooth. The respiratory apparatus can include an expiratory tube configured to receive an expiratory gases flow from a patient. The expiratory tube can include an expiratory inlet, an expiratory outlet, and a wall enclosing an expiratory central bore. The inner wall of the expiratory tube can be corrugated. The wall of the expiratory tube can be permeable to water vapor and substantially impermeable to liquid and bulk flow of the exhaled gases flowing therethrough.

The wall of the expiratory tube can comprise a foamed polymer that is permeable to water vapor and substantially impermeable to liquid water and bulk flow of the exhaled gases. The inspiratory tube can comprise at least one heating element within its central bore. The inspiratory tube can comprise at least one heating element attached to its inner wall. The inspiratory tube can comprise at least one heating element enclosed within its wall. The first elongate member of the inspiratory limb can form in longitudinal cross-section a plurality of bubbles with a flattened surface at the lumen. The inspiratory tube can enclose at least one heating element, and the at least one inspiratory heating element can be between a bubble of the plurality of bubbles and the inspiratory central bore. The expiratory tube can comprise at least one heating element within the expiratory central bore. The expiratory tube can comprise at least one heating element attached to its inner wall. The expiratory tube can comprise at least one heating element embedded within its inner wall. The expiratory tube can comprise a plurality of reinforcing ribs circumferentially arranged around the inner surface and generally longitudinally aligned between the inlet and the outlet. The respiratory apparatus can comprise a control system configured to deliver power to the heater of the humidifier and the at least one heating element.

A breathing circuit can comprise the combination of a smooth bore inspiratory tube with a corrugated, vapor permeable expiratory tube to increase the vapor in humidified gases delivered to a patient via the inspiratory limb of the circuit and increase the removal of vapor from expiratory gases in the expiratory limb of the circuit without increasing the overall resistance to flow of the tubes, thus avoiding increase of the pressure drop in the breathing circuit. The smooth bore inspiratory tube can provide an opportunity for a tradeoff. The smooth bore can reduce the resistance to flow, which can allow for a reduction in the diameter or cross-sectional area of the inspiratory tube while maintaining an acceptable resistance to flow. This reduction in diameter or cross-sectional area of the inspiratory tube reduces the compressible volume of the inspiratory tube. The smaller diameter inspiratory tube can reduce the compressible volume of at least a portion of the breathing circuit which reduces the potential for error in delivered tidal volume. A ventilator typically intends to deliver a set volume of gas to the patient (a 'tidal volume') for each breath. Reducing the error in delivered tidal volume can ensure that the patient is receiving the correct gas volume.

Using the combination of a smooth bore inspiratory tube with a corrugated expiratory tube has an unforeseen synergistic effect that improves performance of the breathing circuit and its components beyond expectations. Using a smooth bore inspiratory tube with a smaller internal diameter than a comparable corrugated tube can decrease the compressible volume of the tube. This decrease in compressible volume can ensure the proper volume of gas is delivered to a patient. As described herein, the inspiratory tube with a smaller internal diameter can reduce the overall compressible volume and pneumatic compliance of the breathing circuit. As described herein, the inspiratory tube with a smaller internal diameter can have a reduced compressible volume which can be a tradeoff for an increased compressible volume of the expiratory tube.

Due to practical reasons, the breathing circuit tubing compressible volume and therefore compliance is usually much larger than the patient's lungs. Factors impacting the breathing circuit tubing compressible volume include minimizing resistance to gas flow of the tubing and enabling the tubes to be long enough to manage the patient in the bed space. This is made worse by some lung disease states leading to patients with very stiff, low compliance lungs. Additionally, a low compressible volume due to decrease in length (e.g. a shortened tube) is directly at odds with both usability and breathable expiratory limbs. In practice, long tubes are generally better, such as to enable freedom of movement and positioning of the patient. In practice, higher surface area is generally better in the expiratory limb to increase breathability of the expiratory limbs.

There are potential tradeoffs between components of the breathing circuit in order to maintain a sufficiently low compressible volume. The diameter or cross-sectional area of the inspiratory tube can be reduced. However, decreasing the internal diameter of the inspiratory tube also increases resistance to flow (RTF) in the inspiratory tube. It was discovered that making the interior bore of the inspiratory tube smooth can compensate for this increase in RTF, because a smooth bore decreases RTF compared to a tube with a corrugated bore or another type of non-smooth bore. The use of a smooth bore also has the added benefit of reducing trapping of vapor and condensates. It was also discovered that, if the increased RTF resulting from decreasing the tube's internal diameter is outweighed by the decrease in RTF resulting from using a smooth bore, then there is a net decrease in RTF in the breathing circuit or at least net decrease in RTF in the inspiratory tube. The smooth bore of the inspiratory tube lowers the RTF which allows for the reduction of the diameter of the inspiratory tube which would normally increase the RTF, wherein the smoothness of the bore and the reduction in diameter can be balanced. As described herein the reduction in the diameter or cross-sectional area can reduce the compressible volume. This lowering of the compressible volume of the inspiratory tube can offset an increase of the compressible volume of the expiratory tube, such as by increasing the diameter or cross-sectional area of the expiratory tube. Increasing the diameter or cross-sectional area of expiratory tube creates a greater surface area of the expiratory tube, which increases the vapor permeability of the expiratory tube.

Certain features, aspects, and advantages of the inventive realization related to the compressible volume of the components of the breathing circuit feature a combination of one or more of the following: the decrease of the internal diameter of the inspiratory tube, the smooth bore of the inspiratory tube, the reduced compressible volume of the inspiratory tube, the increase of the compressible volume of the expiratory tube, the increase of the diameter of the expiratory tube, the increase of the surface area of the expiratory tube, and/or the increase of the vapor permeability of the expiratory tube. Certain features, aspects, and advantages of the present disclosure reflect the inventive realization that this net decrease in RTF, due to the smooth bore inspiratory tube, allows for other components of the circuit to be modified without changing the overall compressible volume, overall RTF, and/or overall pressure drop, for the circuit as a whole. The use of a smooth bore inspiratory tube can permit the use of a longer corrugated expiratory tube, which would otherwise increase RTF in the circuit. The increased length of the expiratory tube improves the ability of the tube to remove vapor from expiratory gases, due at least in part to increased residence time. The increased diameter of the expiratory tube can improve the ability of the tube to remove vapor from expiratory gases, due to the increased wall surface area through which the vapor permeates. When the use of the smooth bore inspiratory tube decreases the RTF of the circuit as a whole, the increase in RTF resulting from increasing the length of the expiratory tube may not result in a net increase in RTF, a net increase in compressible volume, and/or a corresponding pressure drop, in the overall circuit. For instance, based on the design, the increased length of the expiratory tube and the decreased diameter of the smooth bore inspiratory tube can be net neutral regarding RTF.

The use of a smooth bore inspiratory tube in a breathing circuit instead of a corrugated, or similarly non-smooth wall tube, may be combined with the use of a wider (larger cross-sectional area or diameter) expiratory tube in the breathing circuit, which decreases RTF. The tradeoff may not be in RTF, which in this case decreases in both tubes. The smooth bore decreases RTF compared to a tube with a corrugated bore or another type of non-smooth bore. The decrease in RTF in the inspiratory tube may, however, be offset by a decrease in diameter or cross-sectional area increasing RTF. The larger cross-sectional area or diameter expiratory tube also decreases RTF. Instead, there can be a tradeoff of compressible volume due to change in diameter or cross-sectional area of the inspiratory tube and the expiratory tube, which decreases in the inspiratory tube but increases in the expiratory tube. The smaller diameter inspiratory tube has a smaller compressible volume. The larger diameter expiratory tube has a larger compressible volume.

A breathing circuit can comprise an inspiratory limb for carrying inspiratory gases to a patient. The inspiratory limb comprises a first elongate member comprising a hollow body spirally wound to form at least in part a first elongate tube having a longitudinal axis, a first lumen extending along the longitudinal axis, and a hollow wall surrounding the lumen. The inspiratory limb further comprises a second elongate member spirally wound and joined between adjacent turns of the first elongate member, the second elongate member forming at least a portion of an inner wall of the lumen of the first elongate tube. The breathing circuit further comprises an expiratory limb for carrying exhaled gases from the patient. The expiratory limb comprises an inlet, an outlet, and a third elongate member comprising a second tube enclosing a second lumen. The second lumen is configured to contain a bulk flow of the exhaled gases and the second tube is permeable to water vapor and substantially impermeable to liquid water and bulk flow of the exhaled gases.

The foregoing breathing circuit can also have one, some, or all of the following properties, as well as any property or properties described in this disclosure. The wall of the expiratory tube can comprise a foamed polymer that is permeable to water vapor and substantially impermeable to liquid water and bulk flow of the exhaled gases. For purposes of this disclosure, any material described as "permeable to water vapor and substantially impermeable to liquid water and bulk flow of gases" (or substantially similar language) is defined herein as a material that allows water vapor molecules to pass through by diffusion, facilitated diffusion, passive transport, active transport, or another similar mechanism for selectively transporting water vapor molecules, but does not have leak paths from one outer major surface of the material to another outer major surface of the material that allow passage of liquid water or bulk flow of gas through the leak paths.

The foamed polymer can comprise a solid thermoplastic elastomer material having cell voids distributed throughout. The first lumen of the inspiratory limb can have a smooth bore. The second elongate member of the inspiratory limb can enclose at least one heating element. The first elongate member of the inspiratory limb may form in longitudinal cross-section a plurality of bubbles with a flattened surface at the lumen. The second elongate member of the inspiratory limb can further comprise at least one heating element, and the at least one inspiratory heating element can be positioned between a bubble of the plurality of bubbles and the inspiratory central bore. The third elongate member of the expiratory limb can be corrugated. The first elongate tube can enclose a heating element within its lumen. The third elongate member of the expiratory limb can enclose a heating element within the second lumen. The third elongate member of the expiratory limb can comprise a heating element attached to the inner wall of the second tube. The third elongate member of the expiratory limb can comprise a heating element embedded in the wall of the second tube. The second tube can have an inner surface adjacent to the second lumen and the expiratory limb can further comprise a plurality of reinforcing ribs circumferentially arranged around the inner surface and generally longitudinally aligned between the inlet and the outlet. The foamed polymer is desirably selected or manufactured such that the solid thermoplastic elastomer material selectively transports water vapor molecules but the cell voids distributed throughout do not form leak paths allowing passage of liquid water or bulk flow of gas through the leak paths.

A device can comprise a breathing circuit. The breathing circuit further comprises an inspiratory tube configured to receive the inspiratory gases flow from a gas source. The inspiratory tube comprises an inspiratory inlet, an inspiratory outlet, and a wall enclosing an inspiratory central bore, wherein the inner wall of the inspiratory tube is smooth. The breathing circuit further comprises an expiratory tube configured to receive an expiratory gases flow from a patient. The expiratory tube comprises an expiratory inlet, an expiratory outlet, and a wall enclosing an expiratory central bore. The inner wall of the expiratory tube is corrugated, and the wall of the expiratory tube is permeable to water vapor and substantially impermeable to liquid and gases flowing therethrough.

The foregoing device can also have one, some, or all of the following properties, as well as any property or properties described in this disclosure. The wall of the expiratory tube can comprise a foamed polymer that is permeable to water vapor and substantially impermeable to liquid water and bulk flow of the exhaled gases. The inspiratory tube can enclose a heating element within its central bore. The inspiratory tube can comprise a heating element attached to its wall. The inspiratory tube can comprise a heating element embedded in its wall. The expiratory tube can comprise a heating element within its central bore. The expiratory tube can comprise a heating element attached to its inner wall. The expiratory tube can comprise a heating element embedded within its inner wall. The inspiratory tube can comprise in longitudinal cross-section a plurality of bubbles with a flattened surface at the lumen. The inspiratory tube can comprise at least one heating element, and the at least one inspiratory heating element can be positioned between a bubble of the plurality of bubbles and the inspiratory central bore.

Further, the expiratory tube can comprise a plurality of reinforcing ribs circumferentially arranged around the inner surface and generally longitudinally aligned between the inlet and the outlet. The breathing circuit can further comprise a humidifier configured to humidify inspiratory gases flow to be delivered to a patient. The humidifier can comprise a humidification chamber configured to store a volume of liquid and configured to be in fluid communication with the inspiratory gases flow, and a heater configured to heat the volume of liquid in the humidification chamber to create vapor such that the inspiratory gases flow is humidified by the vapor.

A respiratory apparatus can comprise a humidifier, an inspiratory tube, and an expiratory tube. The humidifier is configured to humidify an inspiratory gases flow to a patient. The inspiratory tube is configured to receive the inspiratory gases flow from the humidifier. The inspiratory tube comprises an inspiratory inlet, an inspiratory outlet, and a wall enclosing an inspiratory central bore, wherein the inner wall of the inspiratory tube is smooth. The expiratory tube is configured to receive expiratory gases flow from the patient. The expiratory tube comprises an expiratory inlet, an expiratory outlet, and a wall enclosing an expiratory central bore, wherein the expiratory central bore is corrugated, and wherein the wall of the expiratory tube is permeable to water vapor and substantially impermeable to liquid and bulk flow of the exhaled gases flowing therethrough.

The foregoing respiratory apparatus can also have one, some, or all of the following properties, as well as any property or properties described in this disclosure. The inspiratory tube can comprise at least one heating element within its central bore. The inspiratory tube can comprise at least one heating element attached to its inner wall. The inspiratory tube can comprise at least one heating element enclosed within its wall. The expiratory tube can comprises at least one heating element within the expiratory central bore. The expiratory tube can comprise at least one heating element attached to its inner wall. The expiratory tube can comprise at least one heating element embedded within its inner wall. The inspiratory tube can comprise a spirally wound member that forms in longitudinal cross-section a plurality of bubbles with a flattened surface at the inspiratory central bore. The inspiratory tube can enclose at least one heating element, and the at least one inspiratory heating element can be positioned between a bubble of the plurality of bubbles and the inspiratory central bore. The wall of the expiratory tube can comprise a foamed polymer.

A respiratory apparatus can comprise a humidifier, an inspiratory tube, an expiratory tube, and a control system. The humidifier is configured to humidify an inspiratory gases flow to be delivered to a patient. The humidifier comprises a humidification chamber and a heater. The humidification chamber is configured to store a volume of liquid and configured to be fluid communication with the inspiratory gases flow. The heater is configured to heat the volume of liquid in the humidification chamber to create vapor such that the inspiratory gases flow is humidified by the vapor. The inspiratory tube is configured to receive the humidified inspiratory gases flow from the humidifier. The inspiratory tube comprises a wall enclosing an inspiratory central bore, and the central bore of the inspiratory tube is smooth. The inspiratory tube further comprises a spirally wound first elongate member that forms in longitudinal cross-section a plurality of bubbles with a flattened surface at the inspiratory central bore. The bubbles are configured to insulate the inspiratory central bore. The inspiratory tube further comprises a spirally wound second elongate member joined between adjacent turns of the first elongate member. The second elongate member forms at least a portion of the lumen of the first elongate tube and comprises at least one inspiratory heating element embedded within the second elongate member. The expiratory tube is configured to receive an expiratory gases flow from the patient. The expiratory tube comprises a conduit enclosing an expiratory central bore, wherein the expiratory central bore is corrugated, and wherein the conduit is permeable to water vapor and substantially impermeable to liquid flow therethrough. The expiratory tube further comprises at least one expiratory heating element within the expiratory central bore. The control system can be configured to deliver power to the heater of the humidifier. The control system can be configured to deliver power to the at least one inspiratory heating element. The control system can be configured to deliver power to the at least one expiratory heating element. The control system can be configured to deliver power to the heater of the humidifier and the at least one inspiratory heating element. The control system can be configured to deliver power to the heater of the humidifier and the at least one expiratory heating element. The control system can be configured to deliver power to the at least one inspiratory heating element and the at least one expiratory heating element. The control system is configured to deliver power to two or more of the following: the heater of the humidifier, the at least one inspiratory heating element, and the at least one expiratory heating element. The control system is configured to deliver power to the heater of the humidifier, the at least one inspiratory heating element, and the at least one expiratory heating element.

The foregoing respiratory apparatus can also have one, some, or all of the following properties, as well as any property or properties described in this disclosure. The wall of the expiratory tube can comprise a foamed polymer that is permeable to water vapor and substantially impermeable to liquid water and bulk flow of the exhaled gases. The foamed polymer can comprise a solid thermoplastic elastomer material having cell voids distributed throughout. The at least one inspiratory heating element can be between a bubble of the plurality of bubbles and the inspiratory central bore. The respiratory apparatus can further comprise a patient interface assembly between the inspiratory tube and the expiratory tube. The power delivered by the control system can be calculated to provide increased humidification by the humidifier. The power delivered by the control system can be calculated to provide controlled condensate management by the at least one expiratory heating element. The power delivered by the control system can be calculated to provide controlled condensate management by the at least one inspiratory heating element. The power delivered by the control system can be calculated to provide increased humidification by the humidifier and controlled condensate management by the at least one expiratory heating element and the at least one inspiratory heating element. The respiratory apparatus can further comprise a ventilator configured to provide the inspiratory gases flow and receive the expiratory gases flow. The ventilator can be configured to provide a pulsatile inspiratory gases flow to the humidifier. The ventilator can be configured to provide a constant inspiratory gases flow to the humidifier. The ventilator can be configured to provide a bias flow of gases.

A respiratory apparatus can comprise a humidifier, an inspiratory tube, and an expiratory tube. The humidifier is configured to humidify an inspiratory gases flow to a patient. The inspiratory tube is configured to receive the inspiratory gases flow from a gas source. The inspiratory tube comprises an inspiratory inlet, an inspiratory outlet, and a wall enclosing an inspiratory central bore, wherein the inner wall of the inspiratory tube is smooth. The expiratory tube is configured to receive an expiratory gases flow from a patient. The expiratory tube comprises an expiratory inlet, an expiratory outlet, and a wall enclosing an expiratory central bore. The inner wall of the expiratory tube is corrugated, and the wall of the expiratory tube is permeable to water vapor and substantially impermeable to liquid and gases flowing therethrough. The wall of the expiratory tube can comprise a foamed polymer that is permeable to water vapor and substantially impermeable to liquid water and bulk flow of the exhaled gases. The inspiratory tube can comprise at least one heating element within its central bore. The respiratory apparatus can also have one, some, or all of the following properties, as well as any properties described in this disclosure. The inspiratory tube can comprise at least one heating element attached to its inner wall. The inspiratory tube can comprise at least one heating element enclosed within its wall. The first elongate member of the inspiratory limb can form in longitudinal cross-section a plurality of bubbles with a flattened surface at the lumen. The inspiratory tube can enclose at least one heating element, and the at least one inspiratory heating element can be between a bubble of the plurality of bubbles and the inspiratory central bore. The expiratory tube can comprise at least one heating element within the expiratory central bore. The expiratory tube can comprise at least one heating element attached to its inner wall. The expiratory tube can comprise at least one heating element embedded within its inner wall. The expiratory tube can comprise a plurality of reinforcing ribs circumferentially arranged around the inner surface and generally longitudinally aligned between the inlet and the outlet. The respiratory apparatus can further comprise a control system configured to deliver power to the heater of the humidifier and the at least one heating element.

BRIEF DESCRIPTION OF THE DRAWINGS

Certain features, aspects, and advantages of the present disclosure now will be described with reference to the drawings. The drawings and the associated descriptions are provided to illustrate certain features, aspects, and advantages of the present disclosure and not to limit the scope of the disclosure.

FIG. 2A is a side view of a portion of a composite tube.

DETAILED DESCRIPTION

Breathing Circuit Comprising One Or More Medical Tubes

Figure 1:
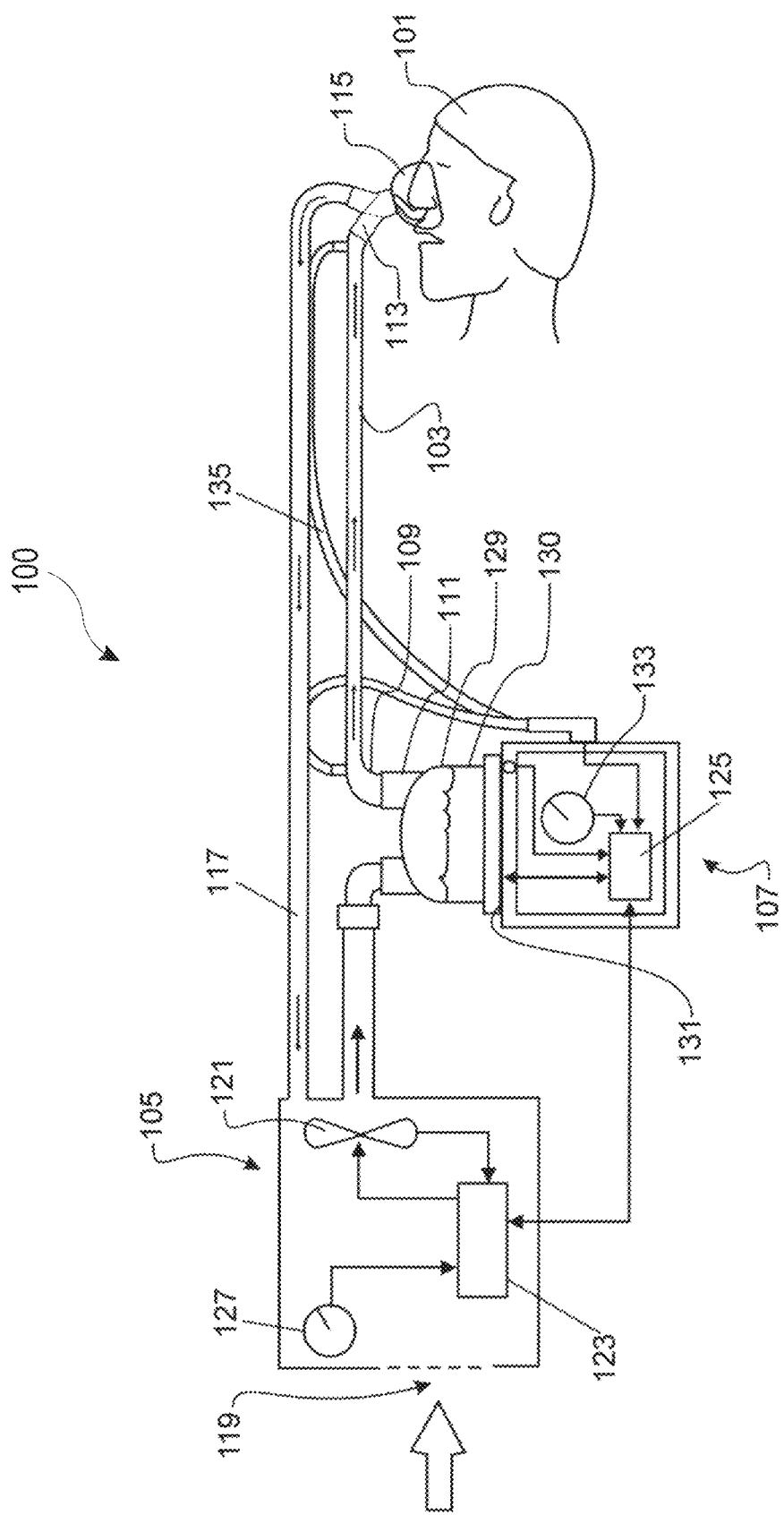
FIG. 1 is a schematic illustration of a breathing circuit incorporating one or more medical tubes.

For a more detailed understanding of the disclosure, reference is first made to FIG. 1, which shows a breathing circuit 100. Such a breathing circuit 100 can be a respiratory humidification circuit. The breathing circuit 100 includes one or more medical tubes. The breathing circuit 100 can include an inspiratory tube 103 and an expiratory tube 117.

As used herein, medical tube is a broad term and is to be given its ordinary and customary meaning to a person of ordinary skill in the art (that is, it is not to be limited to a special or customized meaning) and includes, without limitation, cylindrical and non-cylindrical elongate shapes defining a lumen or comprising a passageway, such as a hollow, elongate body that are configured for use in medical procedures and that otherwise meet applicable standards for such uses. An inspiratory tube is a medical tube that is configured to deliver breathing gases to a patient. An expiratory tube is a medical tube that is configured to move exhaled gases away from a patient.

Gases can be transported in the circuit 100 of FIG. 1. Ambient gases flow from a gases source 105 to a humidifier 107. The humidifier 107 can humidify the gases. The gases source 105 can be a ventilator, a blower or fan, a tank containing compressed gases, a wall supply in a medical facility, or any other suitable source of breathing gases.

The humidifier 107 connects to an inlet 109 (the end for receiving humidified gases) of the inspiratory tube 103 via a port 111, thereby supplying humidified gases to the inspiratory tube 103. The gases flow through the inspiratory tube 103 to an outlet 113 (the end for expelling humidified gases) of the inspiratory tube 103, and then to a patient 101 through a patient interface 115 connected to the outlet 113. The expiratory tube 117 connects to the patient interface 115. The expiratory tube 117 returns exhaled humidified gases from the patient interface 115 to the gases source 105 or to the ambient atmosphere. As used herein, patient interface has a broad meaning and is to be given its ordinary and customary meaning to one of skill in the art, and patient interface also includes, without any limitation, any one or more of a full face mask, a nasal mask, an oral mask, an oral-nasal mask, a nasal pillows mask, nasal cannulas, nasal prongs, a laryngeal mask, or any other suitable coupling between the medical circuit and the airways of the patient.

Gases can enter the gases source 105 through a vent 119. The blower or the fan 121 can cause gases to flow into the gases source 105 by drawing air or other gases through the vent 119. The blower or the fan 121 can be a variable speed blower or fan. An electronic controller 123 can control the blower or fan speed. In particular, the function of the electronic controller 123 can be controlled by an electronic master controller 125. The function can be controlled in response to inputs from the master controller 125 and a user-set predetermined required value (preset value) of pressure or blower or fan speed via a dial or other suitable input device 127.

The humidifier 107 comprises a humidification chamber 129. The humidifier chamber 129 can be configured to contain a volume of water 130 or other suitable humidifying liquid. The humidification chamber 129 can be removable from the humidifier 107. Removability allows the humidification chamber 129 to be more readily sterilized or disposed of after use. The humidification chamber 129 portion of the humidifier 107 can be a unitary construction or can be formed of multiple components that are joined together to define the humidifier chamber 129. The body of the humidification chamber 129 can be formed from a non-conductive glass or plastics material. The humidification chamber 129 can also include conductive components. For instance, the humidification chamber 129 can include a highly heat conductive base (an aluminum base) configured to contact or be associated with a heater plate 131 on the humidifier 107 when the humidification chamber 129 is installed on the humidifier 107.

The humidifier 107 can include electronic controls. The humidifier 107 can include the electronic, analog or digital master controller 125. The master controller 125 can be a microprocessor-based controller executing computer software commands stored in associated memory. In response to the user-set humidity or temperature value input via a user input device 133 and other inputs, the master controller 125 determines when (or to what level) to energize the heater plate 131 to heat the volume of water 130 within the humidification chamber 129.

A temperature probe 135 can connect to the inspiratory tube 103 near the patient interface 115 or the temperature probe 135 can connect to the patient interface 115. The temperature probe 135 can be integrated into the inspiratory tube 103. The temperature probe 135 detects the temperature near or at the patient interface 115. A signal reflecting the temperature can be provided by the temperature probe 135 to the electronic, analog or digital master controller 125. A heating element (not shown) can be used to adjust the temperature of the patient interface 115 and/or the inspiratory tube 103 to raise the temperature of the inspiratory tube 103 and/or the patient interface 115 above the saturation temperature, thereby reducing the opportunity for unwanted condensation.

In FIG. 1, exhaled humidified gases are returned from the patient interface 115 to the gases source 105 via the expiratory tube 117. The expiratory tube 117 can include a vapor permeable material, as described in greater detail below. The vapor permeable expiratory tube can be corrugated.

The expiratory tube 117 can have a temperature probe and/or heating element, as described above with respect to the inspiratory tube 103, to reduce the opportunity for condensation to reach the gases source 105. The expiratory tube 117 need not return exhaled gases to the gases source 105. The exhaled humidified gases can flow directly to ambient surroundings or to other ancillary equipment, such as an air scrubber/filter (not shown).

In FIG. 1, the inspiratory tube 103 includes or comprises a conduit with a smooth bore. The term smooth bore is to be given its ordinary and customary meaning in the art and includes, without limitation, non-corrugated bores, lumens, or passageways. The term "smooth bore" may be used to describe tubes that have an inner surface that does not include significant inner corrugations, annular ribs, bumps, or cavities that significantly influence the flow of gases within the tube. The term "smooth bore" may also be used to describe tubes that do not have repeating inner surface features that disturb a generally laminar flow through the passageway or lumen defined by the smooth bore. The term corrugated is to be given its ordinary and customary meaning in the art and includes, without limitation, having a ridged or grooved surface. Advantageously, the smooth bore causes the conduit to have a lower RTF than a conduit with comparable dimensions having a corrugated bore. A smooth bore reduces the resistance to flow such that the bore (i.e. diameter or cross-sectional area) can be reduced, which results in a lower compressible volume when compared to a corrugated tube having a similar resistance to flow. The inspiratory conduit can be a composite conduit. The composite conduit generally may be defined as a conduit comprising two or more distinct portions, or, more specifically, two or more components that are joined together to define the conduit. The composite conduit can be spirally wound. The composite conduit can be spirally wound in such a way that the two or more components are spirally intertwined or coupled side by side in a spiraling configuration.

The expiratory tube 117 includes or comprises a conduit having at least a portion that is vapor permeable. Vapor permeability facilitates humidity removal. At least the vapor permeable portion of the expiratory tube 117 can be corrugated. The corrugation can be on the inside of the tube. Corrugation increases the inner surface area of the tube. The amount of vapor that can be diffused through a vapor permeable material correlates to the surface area of the material in direct contact with the vapor. Corrugation also increases turbulent flow of gases within the expiratory tube. More turbulent flow means better mixing of the gases, thereby causing the water vapor to travel to the outer walls of the expiratory tube 117. More turbulent flow can increase localized residence in the corrugations in the expiratory tube, which, when coupled with vapor permeability attributes, further improves humidity removal. Increased localized residence time also decreases the temperature of the gases swirling in the "pocket" of each corrugation relative to that of a comparably sized smooth bore tube, which increases the relative humidity of those gases relative to that of a comparably sized smooth bore tube. The increased relative humidity increases the vapor pressure gradient across the wall of the expiratory tube 117 relative to that of a comparably sized smooth bore tube, which in turn increases vapor diffusion through the wall of the corrugated expiratory tube relative to that of a comparably sized smooth bore tube.

A vapor permeable, corrugated conduit can be formed, at least in part, from a foamed polymer that is permeable to water vapor and substantially impermeable to liquid water and bulk flow of gases. The expiratory tube 117 can comprise a wall defining a space within the expiratory tube 117. At least a part of the wall can be formed of a foamed material configured to be permeable to water vapor and substantially impermeable to liquid water and bulk flow of gases.

A vapor permeable expiratory tube 117 can be formed from non-foam based materials. The non-foam based materials can include a helically-wrapped vapor permeable tape. Corrugation of the expiratory tube 117 can be accomplished using non-foam based materials. The non-foam based materials can include beads of varying diameters arranged in an alternating pattern to form a corrugated inner surface.

The inspiratory tube 103 includes a smooth bore conduit. The smooth bore conduit can be heated and insulated to minimize condensate creation and maximize humidity delivery. Decreased condensate formation within the inspiratory tube permits more vapor in humidified gases to be delivered to a patient. Several factors affect condensate creation within the inspiratory tube 103 including the inner bore diameter, the degree of inner bore smoothness, the level of tube insulation, the presence of heating elements (such as wires and elements) associated with the tube 103, and the position of heating elements within the tube 103 (whether heating elements are located within the inner bore of the tube 103 or within the wall of the tube 103). Specifically, decreasing the inner bore diameter of the inspiratory tube 103 increases gases velocity as gases travel through the inspiratory tube 103. Increasing the smoothness of the bore decreases turbulence and creates a more parabolic wavefront across the inner wall of the lumen. Therefore, decreasing the inner bore diameter and making the inner bore smooth causes the faster gases located near the center of the tube to transfer less heat to the slower gases located near the tube wall. A smooth bore tube also provides no pockets in which vapor could be trapped or condensate might pool, as a corrugated tube would have. The vapor carried by the gases is therefore encouraged to exit the tube and thus be delivered to the patient.

Increasing the degree of tube insulation reduces heat loss across the wall of the inspiratory tube 103, which maximizes humidity delivery by minimizing condensation formation. Adding increased insulation to the inspiratory tube 103 also makes the breathing circuit 100 more efficient by decreasing how hard a heating element must work to maintain a target temperature and humidity because the insulated tube will better maintain the temperature and absolute humidity of the gases as they travel through the tube.

Figure 2B:
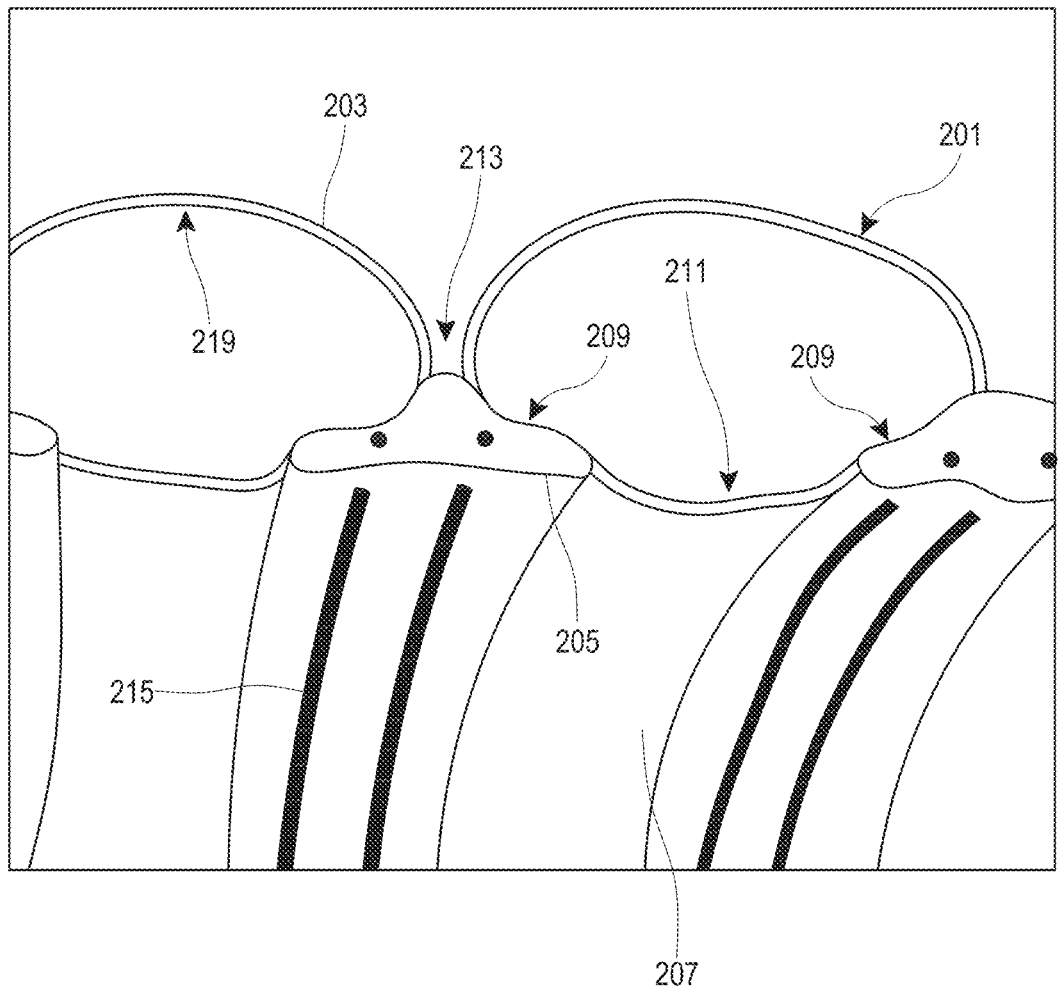
FIG. 2B is a longitudinal cross-section of the composite tube of FIG. 2A.

Adding heating elements to the inspiratory tube 103 also maximizes humidification delivery and decreases condensation. Positioning one or more heating elements within the wall of the inspiratory tube 103 maximizes humidification, minimizes condensate formation, and contributes to the efficiency of the inspiratory tube 103, the breathing circuit 100, or the humidification system. When located within the wall of the inspiratory tube 103, the heating element heats the wall while not directly heating the gases. Heating the wall reduces the relative humidity (heating gases increases the temperature, which reduces the relative humidity) of gases near the wall. Positioning the heating element on the lumen side of an inner wall of insulating "bubbles" (defined below) of an inspiratory tube 103 (described in greater detail below) can further reduce heat loss outward through the wall of the inspiratory tube 103, which in turn maximizes humidification while minimizing condensate creation. As used herein, the term "bubble" refers to the cross-sectional shape of the hollow body formed from an elongated wind or turn of the first elongate member 203, taken in transverse cross-section through the wind or turn, for example as shown in FIG. 2B. As used herein, any reference to "bubble" means an elongate hollow body that, in cross-section, has a shape defined by a wall with a hollow space within. Such shapes could include an oval or "D" shape, with reference to FIG. 2B. Such shapes could include, without limitation, "O" shapes, and other regular and irregular shapes, symmetric and asymmetric.

The expiratory tube 117 can include a corrugated conduit to maximize vapor removal while minimizing condensate formation and increasing localized residence time in the corrugations. The expiratory tube 117 can include a vapor permeable conduit to maximize vapor removal. The expiratory tube 117 can include a heated conduit to maximize vapor removal while minimizing condensate formation. The expiratory tube 117 can include a corrugated, vapor permeable, and/or heated conduit to maximize vapor removal while minimizing condensate formation and increasing localized residence time in the corrugations. Decreased condensate formation within the expiratory tube 117 permits more vapor to diffuse across the wall of the expiratory tube 117. The presence of a heating element can maintain the relative humidity of the gases below 100% (that is, maintain the gases temperature above the dewpoint saturation temperature). Positioning the heating element near or within the wall of the expiratory tube 117 causes heating of the gases near the wall of the expiratory tube 117. Keeping the gases temperature near the wall of the expiratory tube 117 above dewpoint avoids or limits condensate formation. The inspiratory tube 103 and the expiratory tube 117 are described in even greater detail elsewhere in this specification.

Referring back to FIG. 1, the gases source 105 typically intends to deliver a set volume of gas to the patient 101 for each breath. This set volume can be referred to as a tidal volume. It is desired that the patient 101 receives the correct gas volume in order to reduce the likelihood of risk of lung injury and to increase the likelihood of sufficient ventilation. When a gases source 105, such as a ventilator, creates a breath for a patient, the gases source 105 must fill both the patient lung and the breathing circuit 100, which can include the filter, the supply tube from the ventilator to the humidifier, the humidifier chamber, the inspiratory tube, the expiratory tube, and any other components shown or described with respect to FIG. 1. Therefore, the gases source 105 must estimate or otherwise account for the gas used to fill the breathing circuit 100 and compensate for this to increase the likelihood of accurate delivery of gas volume to the patient.

The gases source 105 can conduct a test for pneumatic compliance of the breathing circuit 100. In this test, the gases source 105 is attempting to determine the volume required to create a specific pressure. Pneumatic compliance is dependent on at least compressible volume. The lower the compressible volume of the breathing circuit 100, the lower the pneumatic compliance of the breathing circuit 100 for a fixed extensibility. The lower the pneumatic compliance of a breathing circuit relative to the patient lung compliance, the less potential there is for error in delivered tidal volume. If a measurement of pneumatic compliance of the breathing circuit is incorrect by a small amount and the pneumatic compliance of the breathing circuit is large in comparison to the patient's lung compliance, then the percentage error in delivered tidal volume to the patient will become very large. For example, if a measurement of pneumatic compliance of the breathing circuit is incorrect by 5%, and the pneumatic compliance of the breathing circuit is large in comparison to the patient's lung compliance, then the percentage error in delivered tidal volume to the patient is potentially much larger than 5%.

Figure 1A:
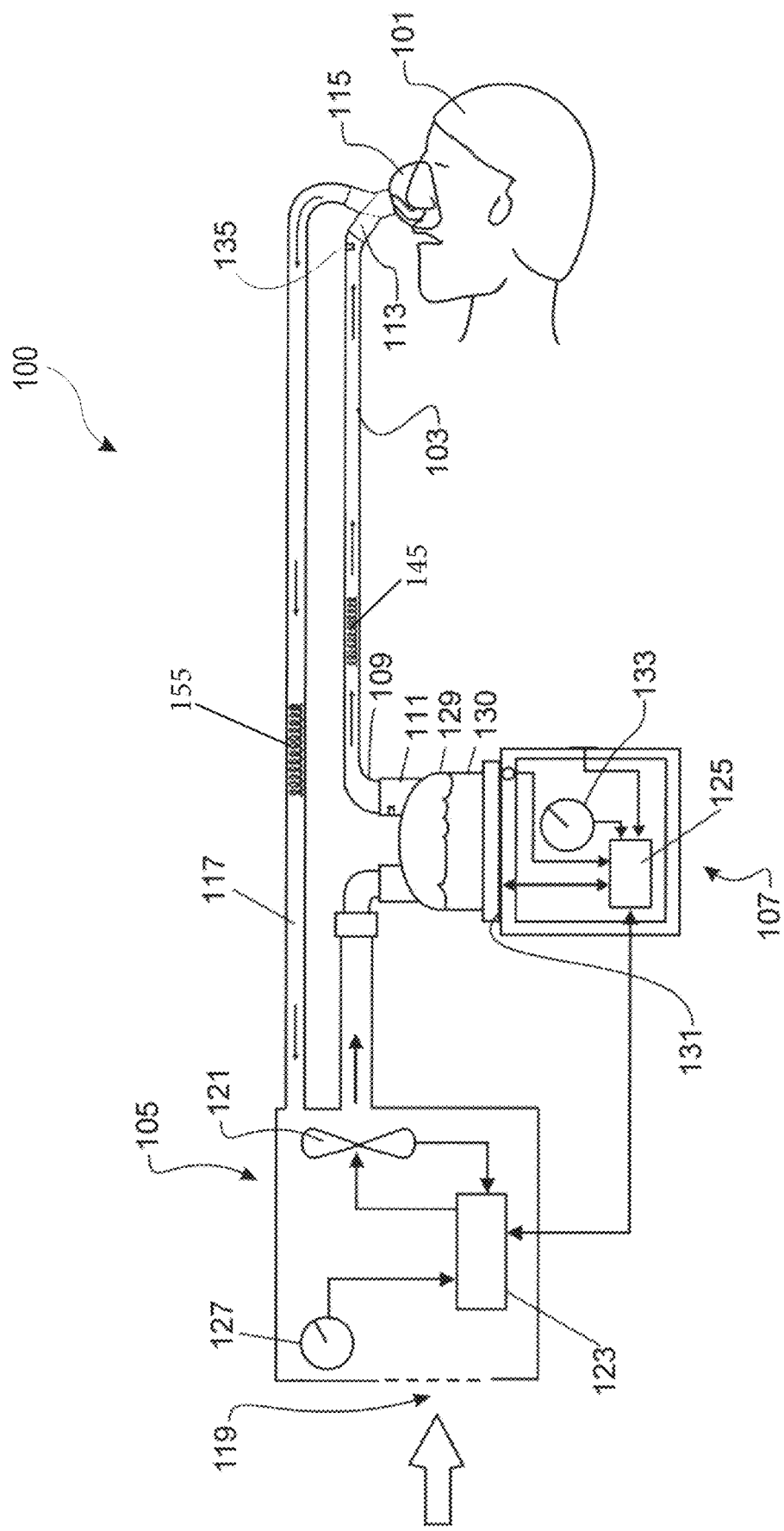
FIG. 1A is a schematic illustration of a breathing circuit incorporating one or more medical tubes.
Figure 1B:
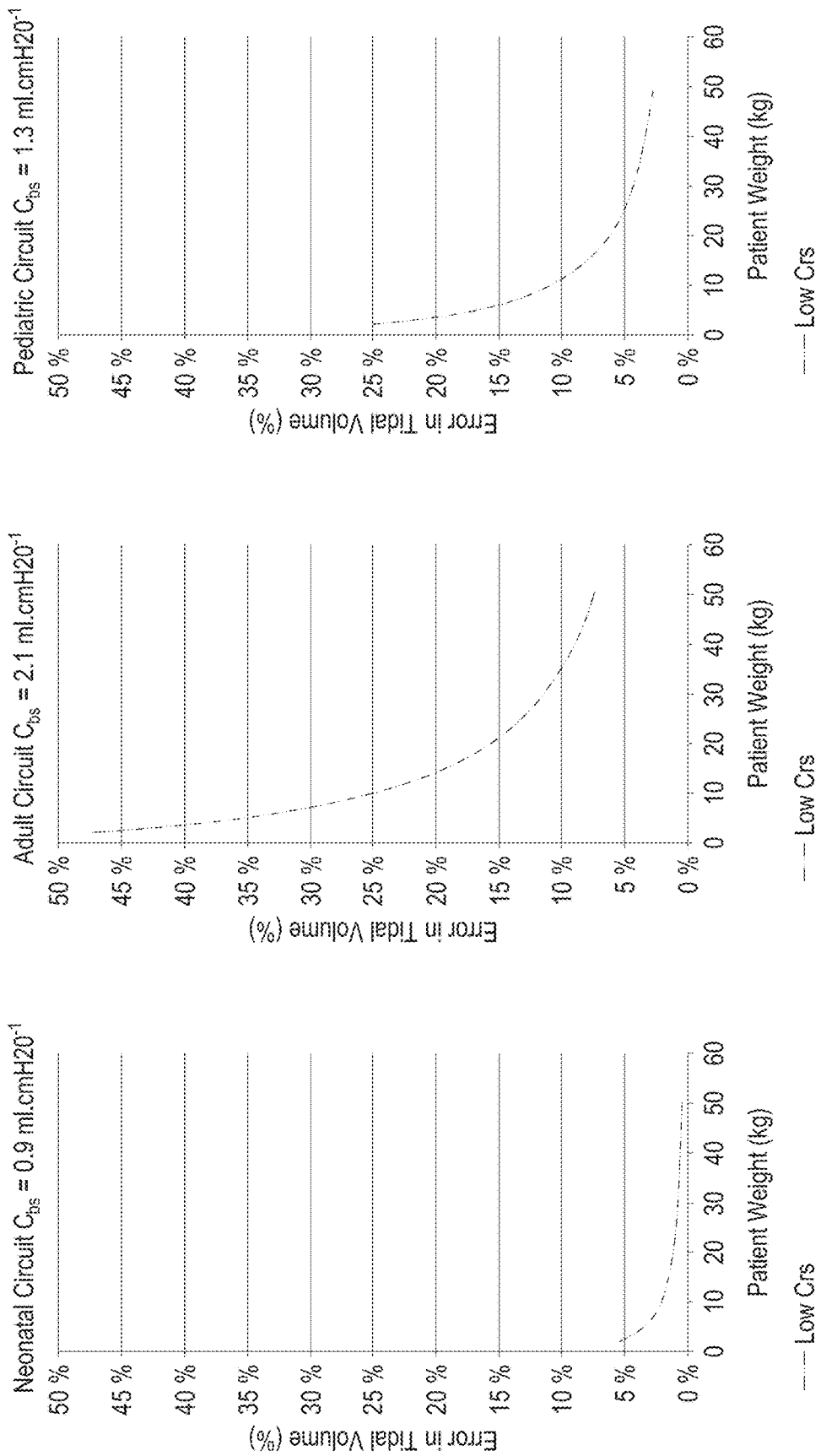
FIG. 1B shows three graphs demonstrating an impact of breathing circuit compliance on tidal volume error.

FIG. 1B illustrates three graphs. The graphs of FIG. 1B demonstrate the error in delivered tidal volume with a theoretical 10% error introduced in the gases source measurement of breathing circuit pneumatic compliance. The three graphs are for three different circuit compliance specifications (e.g., neonatal, adult and pediatric). For the neonatal circuit, the breathing circuit compliance ($C_{bs}$) equals 0.9 ml·cmH2O$^{-1}$. For the adult circuit, the breathing circuit compliance ($C_{bs}$) equals 2.1 ml·cmH2O$^{-1}$. For the pediatric circuit, the breathing circuit compliance ($C_{bs}$) equals 1.3 ml·cmH2O$^{-1}$. Each graph shows the error in delivered tidal volume for a patient with low respiratory system compliance.

It has been discovered that the error dramatically increases as the patient's weight decreases. The patient's weight is correlated to the intended tidal volume. As the patient's weight decreases, the intended tidal volume decreases. Comparing the graphs of FIG. 1B illustrates that, for a given tidal volume, the error is larger if the breathing circuit compliance is larger. It has been discovered that it is desirable to keep the overall compressible volume and compliance of the breathing circuit as low as possible in relation to the lung characteristics of the patients intended to be receiving treatment.

Due to practical reasons, such as minimizing resistance to gas flow of the tubing and enabling the tubes to be long enough to manage the patient in the bed space, the breathing circuit tubing compressible volume and therefore compliance is usually much larger than the patient's lungs. This difference is made greater by some lung disease states leading to patients with very stiff, low compliance lungs. A low compressible volume, which can result from short tubes, can be disadvantageous from a usability perspective. Longer tubes, and breathable expiratory limbs, which benefit from higher surface area, can be disadvantageous from a compressible volume perspective.

The relevance of compressible volume is that there can be a tradeoff between components of the breathing circuit in maintaining a sufficiently low compressible volume. The smooth bore of the inspiratory tube 103 lowers the resistance to flow, which allows the reduction in the diameter of the inspiratory tube 103 and therefore a reduction in the compressible volume. This lowering of the compressible volume of the inspiratory tube 103 allows for an increase the compressible volume of the expiratory tube 117 by increasing the diameter. Increasing the diameter of expiratory tube 117 creates a greater surface area of the expiratory tube 117, which increases the vapor permeability of the tube 117.

It was realized that incorporating the inspiratory tube 103 with a smaller diameter, smooth bore conduit in conjunction with the expiratory tube 117 with a corrugated conduit allows the expiratory tube 117 to be larger in diameter and/or longer than otherwise would be possible while maintaining the overall system compressible volume. Additionally or alternatively, the combination of the smaller diameter, smooth bore inspiratory tube 103 and the larger diameter, corrugated expiratory tube 117 can maintain the overall pressure drop. Additionally or alternatively, the combination of the smaller diameter, smooth bore inspiratory tube 103 and the larger diameter, corrugated expiratory tube 117 can maintain the resistance to flow (RTF) of the breathing circuit 100 at a desirable level. Ordinarily, increasing the length of a conduit undesirably increases the compressible volume of the conduit, and therefore, the compressible volume of the overall breathing circuit. Ordinarily, increasing the length of a conduit undesirably increases the RTF of the conduit, and therefore, increases the RTF of the overall breathing circuit. On the other hand, when the conduit is vapor permeable, the increased length advantageously improves the conduit's ability to remove vapor from exhaled gases. It was discovered that the combination of the inspiratory tube 103 with a smaller diameter, smooth bore and the expiratory tube 117 with a corrugated, vapor-permeable, larger diameter conduit increases the ability of the expiratory tube 117 to remove water vapor from the breathing circuit without increasing the overall system compressible volume, pressure drop, and/or RTF.

It was further realized that incorporating the inspiratory tube 103 with a smooth bore conduit in conjunction with the expiratory tube 117 with a corrugated conduit allows the humidifier 107 to increase humidity performance providing a therapeutic benefit to patients, while driving closer to fully saturated gases, without adding the risk of liquid damage to the gases source 105 or condensate draining back to patient.

The inspiratory tube 103 with a smooth bore, spiral wound conduit can be paired with the expiratory tube 117 with a corrugated, vapor permeable conduit. As discussed above, the smooth bore of the inspiratory tube 103 has lower RTF than a similarly sized corrugated bore. It can also have a smaller internal diameter than a corrugated conduit. Ordinarily, decreasing internal diameter reduces compressible volume and undesirably increases the inspiratory tube's RTF. Nevertheless, the smooth bore characteristics can be selected such that the reduction in RTF associated with the smooth bore of the inspiratory tube 103 outweighs the RTF increase resulting from the smaller internal diameter of the inspiratory tube 103. This selection of a smaller diameter inspiratory tube 103 also reduces the compressible volume of the inspiratory tube 103. This selection then allows the corrugated expiratory tube 117 paired with the smooth bore inspiratory tube 103 to be longer and/or have a greater diameter or cross-sectional area without increasing the overall system pressure drop or compressible volume. The increased length of the expiratory tube 117 ordinarily undesirably increases the RTF and compressible volume of the tube. However, the increased length also improves the ability of the vapor permeable tube to remove vapor from expiratory gases. In this arrangement, pairing the smooth bore inspiratory tube 103 with the corrugated expiratory tube 117 enhances the performance of the expiratory tube 117. The system pressure drop of a breathing circuit as might exist from ventilator outlet to ventilator inlet can be affected by the pressure characteristics (RTF) of each element in the circuit. Referring back to FIG. 1, assuming the pressure characteristics of the supply tube from ventilator to humidifier, humidifier chamber, interface tube, and interface body are fixed, the primary factors contributing to system pressure drop are the resistance to flow and dimensions (length and diameter) of the inspiratory tube 103 and the expiratory tube 117. Any change to one of these factors should advantageously be balanced by other factor(s) to avoid increasing the system pressure drop, RTF and/or compressible volume. As described herein, the primary factors contributing to compressible volume are the tube profile, extensibility, and dimensions (length and diameter or cross-sectional area) of the inspiratory tube 103 and the expiratory tube 117. There can be a tradeoff between decreasing the compressible volume of the inspiratory tube 103 and increasing the compressible volume of the expiratory tube 117 while maintaining the compressible volume of the breathing circuit. As described herein, increasing the compressible volume of the expiratory tube 117 has advantages in in vapor permeability in the expiratory limb.

The smooth bore of the inspiratory tube 103 can reduce resistance to flow (as compared to a corrugated inspiratory tube), decreasing the overall system pressure drop. This allows any or all of the other three factors (resistance to flow of the corrugated expiratory tube 117 or dimensions of either tube) to be altered in a way that increases the system pressure drop. The internal diameter of the inspiratory tube 103 can be smaller than the comparable corrugated inspiratory tube, which desirably increases the velocity of the gases flowing through the inspiratory tube 103. However, the smaller diameter also adds back some resistance to flow. So long as the RTF increase caused by the smaller diameter is sufficiently smaller than the RTF decrease caused by the use of the smooth bore, the length of the corrugated expiratory tube 117 can be increased without increasing the system pressure drop. Increasing the length of the expiratory tube 117 increases the surface area of the tube wall of the expiratory tube 117. The amount of vapor that can be diffused through a vapor permeable material is correlated to the surface area of the material. Increasing the length of the expiratory tube 117 increases the surface area of the wall of the expiratory tube 117 and also increases the residence time of gases in the expiratory tube 117. The amount of vapor that can be diffused through a permeable material is also correlated to the length of time the vapor-carrying gases are in contact with the material.

The compressible volume of the breathing circuit (the cumulative volume of the entire gases flow path) can also be balanced in the same way. For instance, a change in dimensions (cross-sectional area or diameter, length) of the inspiratory tube 103 can offset a change in dimensions (cross-sectional area or diameter, length) of the corrugated expiratory tube 117. As described herein, the decrease in diameter of the inspiratory tube 103 can decrease compressible volume. This decrease in compressible volume can improve accuracy of the delivered tidal volume. As described herein, the decrease in diameter of the inspiratory tube 103 can offset an increased diameter and/or an increased length of the expiratory tube 117. As described herein, the change in dimensions of the expiratory tube 117 can facilitate the function of the expiratory tube 117, such as by increasing vapor permeability of the expiratory tube 117. Altering tube dimensions affects both the system pressure drop and the system compressible volume, so both equations should advantageously be balanced or selected simultaneously when making changes. Reducing the diameter of the inspiratory tube 103 can both increase resistance to flow and decrease compressible volume, while increasing the average gases velocity through the tube. Adding to the length of the corrugated expiratory tube 117 both increases resistance to flow and increases compressible volume. Table 1 summarizes the impacts of various features on these two system metrics:

TABLE 1

| Feature | Effect | Pressure drop | Compressible volume |
|---|---|---|---|
| Inspiratory length | Shorter: decreases residence time, decreasing condensation (but too short impacts usability) | Decreases | Decreases |
| Inspiratory diameter | Narrower: decreases residence time, decreasing condensation | Increases | Decreases |
| Expiratory length | Longer: increases surface area and residence time, both increasing vapor diffusion | Increases | Increases |
| Expiratory diameter | Wider: increases surface area and residence time, both increasing vapor diffusion | Decreases | Increases |
| Inspiratory bore surface | Smooth: decreases turbulence, decreasing condensation | Decreases | No change |
| Expiratory bore surface | Corrugated: increases turbulence, increasing vapor diffusion | Increases | No change |

Pairing the corrugated expiratory tube 117 with the smooth bore inspiratory tube 103 enables higher performance of the inspiratory tube 103. Pairing the larger diameter expiratory tube 117 with the smaller bore inspiratory tube 103 can be net neutral for compressible volume, but increase functionality of the breathing circuit (e.g., increase vapor diffusion in the expiratory tube 117). In this arrangement, the smooth bore inspiratory tube 103 minimizes condensate creation, and therefore maximizes humidity delivery. The overall compressible volume can be decreased by changes in the dimensions, such as diameter and length of the inspiratory tube 103 and expiratory tube 117. In some arrangements, the inspiratory tube 103 is insulated, which helps to make the humidifier 107 and/or a heating element, such as the heater plate 131, more efficient in producing humidity that is delivered to the patient 101. The heater plate 131 does not have to work as much because it does not have to produce a high target temperature at the humidification chamber port 111, and this is because the heated and insulated inspiratory tube 103 will better maintain the absolute humidity of the gases flowing from the humidification chamber port 111 and through the inspiratory tube 103.

The location of a heater wire in the wall of the inspiratory tube 103 also increases the efficiency of the inspiratory tube 103 in maintaining the relative humidity of the gas. The heater wire can heat the wall of the inspiratory tube 103, not the gases flowing through the lumen of the inspiratory tube 103, which reduces the relative humidity of the gases near the wall of the inspiratory tube 103. When the inspiratory tube 103 includes a composite conduit with a spiral wound hollow body or "bubble" tube (described in greater detail below), the heater wire is under (on the lumen side of an inner wall) the insulating bubble, which reduces heat loss outward through the wall of the inspiratory tube 103.

The smooth bore inspiratory tube 103 promotes laminar gases flow, which creates a more parabolic wavefront across the lumen of the inspiratory tube 103, with the gases closer to the center of the lumen having a higher velocity relative to gases closer to the wall of the inspiratory tube 103. In this arrangement, the higher velocity gases have less time during transit from the inlet 109 to the outlet 113 to transfer heat to neighboring lower velocity gases. Combined with the inward direction of the heat generated by the heater wire, this arrangement helps to further increase the heat retained by the gases flow.

The smooth bore inspiratory tube 103 also provides no pockets in which vapor could be trapped or condensate might pool, as a corrugated tube would have. The vapor carried by the gases is therefore encouraged to remain in vapor phase and exit the inspiratory tube 103 and thus be delivered to the patient 101.

The corrugated expiratory tube 117 maximizes vapor removal and minimizes condensate formation. The expiratory tube 117 can be vapor permeable which promotes diffusion of vapor through the wall of the expiratory tube 117 to the outside atmosphere. In some arrangements, the expiratory tube 117 is vapor permeable and heated; the control of the heating along the tube promotes diffusion of vapor through the wall of the expiratory tube 117 to the outside atmosphere. Vapor transferred to the outside atmosphere will not be delivered to the gases source 105. The corrugated expiratory tube 117 creates turbulence in the portion of the gases flow adjacent the wall of the expiratory tube 117, which increases the residence time of gases adjacent the wall in the corrugations. Increased residence time increases the opportunity for vapor diffusion through the wall of the expiratory tube 117. Increased residence time also decreases the temperature of the gases swirling in the "pocket" of each corrugation, which increases the relative humidity of those gases. The increased relative humidity increases the vapor pressure gradient across the wall of the expiratory tube 117, which in turn increases vapor diffusion through the wall.

As discussed below, the expiratory tube 117 can include a heater wire coiled near the center of the lumen of the expiratory tube 117. The heater wire, so positioned, adds to the turbulence of the gases flow and while minimizing condensate formation. More turbulence means better mixing of the gases, thereby causing the water vapor to travel to the outer walls of the expiratory tube 117. The corrugated expiratory tube 117 also provides corrugation "pockets" that have the advantage of collecting any liquid that condenses from vapor. Liquid pooled in the corrugations is liquid not delivered to the gases source 105. In some arrangements, the heater wire can be positioned in the wall of the expiratory tube 117. The presence of a heater wire in the expiratory tube 117 also minimizes condensate formation within the expiratory tube.

The combination of the smooth bore inspiratory tube 103 with the corrugated expiratory tube 117 allows the humidifier 107 to increase humidity performance. There is a contribution from the patient and bias flow in both invasive and non-invasive ventilation. In both, the expiratory tube 117 can function to decrease the amount of humidity returned to the gases source 105. The function of the expiratory tube 117 can be to sufficiently reduce the amount of humidity returned to the gases source 105.

The function of the expiratory tube can enable the humidifier 107 and the inspiratory tube 103 to deliver higher levels of humidity to the patient 101. If the expiratory tube 117 could not sufficiently reduce the amount of humidity returned to the gases source 105, the ability of the humidifier 107 and the inspiratory tube 103 to deliver higher levels of humidity to the patient 101 would have to be reduced or dialed back, because some of that extra humidity would be carried through the expiratory tube 117 to the gases source 105.

FIG. 1A shows a breathing circuit 100, which can be similar to FIG. 1 described herein. Such a breathing circuit 100 can be a respiratory humidification circuit. The breathing circuit 100 includes one or more medical tubes. The breathing circuit 100 can include an inspiratory tube 103 and an expiratory tube 117.

Gases can be transported in the circuit 100 of FIG. 1A. Ambient gases flow from a gases source 105 to a humidifier 107. The humidifier 107 can humidify the gases. The gases source 105 can be a ventilator, a blower or fan, a tank containing compressed gases, a wall supply in a medical facility, or any other suitable source of breathing gases.

The humidifier 107 connects to an inlet 109 (the end for receiving humidified gases) of the inspiratory tube 103 via a port 111, thereby supplying humidified gases to the inspiratory tube 103. The gases flow through the inspiratory tube 103 to an outlet 113 (the end for expelling humidified gases) of the inspiratory tube 103, and then to a patient 101 through a patient interface 115 connected to the outlet 113. The expiratory tube 117 connects to the patient interface 115. The expiratory tube 117 returns exhaled humidified gases from the patient interface 115 to the gases source 105 or to the ambient atmosphere.

Gases can enter the gases source 105 through a vent 119. The blower of the fan 121 can cause gases to flow into the gases source 105 by drawing air or other gases through the vent 119. The blower or the fan 121 can be a variable speed blower or fan. An electronic controller 123 can control the blower or fan speed. In particular, the function of the electronic controller 123 can be controlled by an electronic master controller 125. The function can be controlled in response to inputs from the master controller 125 and a user-set predetermined required value (preset value) of pressure or blower or fan speed via a dial or other suitable input device 127.

The humidifier 107 comprises a humidification chamber 129. The humidifier chamber 129 can be configured to contain a volume of water 130 or other suitable humidifying liquid. The humidification chamber 129 can be removable from the humidifier 107. Removability allows the humidification chamber 129 to be more readily sterilized or disposed of after use. The humidification chamber 129 portion of the humidifier 107 can be a unitary construction or can be formed of multiple components that are joined together to define the humidification chamber. The body of the humidification chamber 129 can be formed from a non-conductive glass or plastics material. The humidification chamber 129 can also include conductive components. For instance, the humidification chamber 129 can include a highly heat conductive base (an aluminum base) configured to contact or be associated with a heater plate 131 on the humidifier 107 when the humidification chamber 129 is installed on the humidifier 107.

The humidifier 107 can include electronic controls. The humidifier 107 can include the electronic, analog or digital master controller 125. The master controller 125 can be a microprocessor-based controller executing computer software commands stored in associated memory. In response to the user-set humidity or temperature value input via a user input device 133 and other inputs, the master controller 125 determines when (or to what level) to energize the heater plate 131 to heat the volume of water 130 within the humidification chamber 129.

As discussed above, any suitable patient interface can be used for the patient interface 115. A temperature probe 135 can connect to the inspiratory tube 103 near the patient interface 115 or the temperature probe 135 can connect to the patient interface 115. The temperature probe 135 can be integrated into the inspiratory tube 103. The temperature probe 135 detects the temperature near or at the patient interface 115. A signal reflecting the temperature can be provided by the temperature probe 135 to the electronic, analog, or digital master controller 125. A heating element (not shown) can be used to adjust the temperature of the patient interface 115 to raise the temperature of the patient interface 115 above the saturation temperature, thereby reducing the opportunity for unwanted condensation. A heating element 145 can also be used to adjust the temperature of the inspiratory tube 103 to raise the temperature of the inspiratory tube 103 above the saturation temperature, thereby reducing the opportunity for unwanted condensation.

In FIG. 1A, exhaled humidified gases are returned from the patient interface 115 to the gases source 105 via the expiratory tube 117. The expiratory tube 117 can include a vapor permeable material, as described in greater detail below. The vapor permeable expiratory tube can be corrugated.

The expiratory tube 117 can have a temperature probe and/or heating element, as described above with respect to the inspiratory tube 103, to reduce the opportunity for condensation to reach the gases source 105. The expiratory tube 117 need not return exhaled gases to the gases source 105. The exhaled humidified gases can flow directly to ambient surroundings or to other ancillary equipment, such as an air scrubber/filter (not shown).

In FIG. 1A, the inspiratory tube 103 includes or comprises a conduit with a smooth bore. The smooth bore causes the inspiratory tube 103 to have a lower RTF than a conduit with comparable dimensions having a corrugated bore. A smooth bore reduces the resistance to flow such that the bore (i.e. diameter or cross-sectional area) can be reduced, which results in a lower compressible volume when compared to a corrugated tube having a similar resistance to flow. The inspiratory conduit can be a composite conduit. The composite conduit generally may be defined as a conduit comprising two or more distinct portions, or, more specifically, two or more components that are joined together to define the conduit. The composite conduit can be spirally wound. The composite conduit can be spirally wound in such a way that the two or more components are spirally intertwined or coupled side by side in a spiraling configuration.

The expiratory tube 117 includes or comprises a conduit having at least a portion that is vapor permeable. Vapor permeability facilitates humidity removal. At least the vapor permeable portion of the expiratory tube 117 can be corrugated. The corrugation can be on the inside of the tube. Corrugation increases the inner surface area of the tube. The amount of vapor that can be diffused through a vapor permeable material correlates to the surface area of the material in direct contact with the vapor. Corrugation also increases turbulent flow of gases within the expiratory tube. More turbulent flow means better mixing of the gases, thereby causing the water vapor to travel to the outer walls of the expiratory tube 117. More turbulent flow can increase localized residence time in the corrugations in the expiratory tube, which, when coupled with vapor permeability attributes, further improves humidity removal. Increased residence time in the corrugation also decreases the temperature of the gases swirling in the "pocket" of each corrugation relative to that of a comparably sized smooth bore tube, which increases the relative humidity of those gases relative to that of a comparably sized smooth bore tube. The increased relative humidity increases the vapor pressure gradient across the wall of the expiratory tube 117 relative to that of a comparably sized smooth bore tube, which in turn increases vapor diffusion through the wall of the corrugated expiratory tube relative to that of a comparably sized smooth bore tube.

A vapor permeable, corrugated conduit can be formed, at least in part, from a foamed polymer that is permeable to water vapor and substantially impermeable to liquid water and bulk flow of gases. The expiratory tube 117 can comprise a wall defining a space within the expiratory tube 117. At least a part of the wall can be formed of a vapor permeable foamed material configured to allow the transmission of water vapor but to substantially prevent the transmission of liquid water and bulk flow of gases.

A vapor permeable expiratory tube 117 can be formed from non-foam based materials. The non-foam based materials can include a helically-wrapped vapor permeable tape. Corrugation of the expiratory tube 117 can be accomplished using non-foam based materials. The non-foam based materials can include beads of varying diameters arranged in an alternating pattern to form a corrugated inner surface.

The inspiratory tube 103 includes a smooth bore conduit. The smooth bore conduit can be heated and insulated to minimize condensate creation and maximize humidity delivery. Decreased condensate formation within the inspiratory tube permits more vapor in humidified gases to be delivered to a patient. Several factors affect condensate creation within the inspiratory tube 103 including the inner bore diameter, the degree of inner bore smoothness, the level of tube insulation, the presence of heating elements 145 (such as wires and elements) associated with the tube 103, and the position of heating elements within the tube 103, whether heating elements are located within the inner bore of the tube 103 or within the wall of the tube 103. Specifically, decreasing the inner bore diameter of the inspiratory tube 103 increases gases velocity as gases travel through the inspiratory tube 103. Increasing the smoothness of the bore decreases turbulence and creates a more parabolic wavefront across the lumen. Therefore, decreasing the inner bore diameter and making the inner bore smooth causes the faster gases located near the center of the tube to transfer less heat to the slower gases located near the tube wall. A smooth bore tube also provides no pockets in which vapor could be trapped or condensate might pool, as a corrugated tube would have. The vapor carried by the gases is therefore encouraged to exit the tube and thus be delivered to the patient.

Increasing the degree of tube insulation reduces heat loss across the wall of the inspiratory tube 103, which maximizes humidity delivery and minimizes condensate formation. Adding increased insulation to the inspiratory tube 103 also makes the breathing circuit 100 more efficient by decreasing how hard a heating element must work to maintain a target temperature and humidity because the insulated tube will better maintain the temperature and absolute humidity of the gases as they travel through the tube.

Adding heating elements to the inspiratory tube 103 also maximizes humidification and decreases condensation. Positioning one or more heating elements within the wall of the inspiratory tube 103 maximizes humidification, minimizes condensate formation, and contributes to the efficiency of the inspiratory tube 103, the breathing circuit 100, or the humidification system. When located within the wall of the inspiratory tube 103, the heating element heats the wall while not directly heating the gases. Heating the wall reduces the relative humidity (heating gases increases the temperature, which reduces the relative humidity) of gases near the wall. Positioning the heating element 145 on the lumen side of an inner wall of the insulating "bubbles" (defined elsewhere) of an inspiratory tube 103 (described in greater detail below) can further reduce heat loss outward through the wall of the inspiratory tube 103, which in turn maximizes humidification while minimizing condensate creation.

The expiratory tube 117 can include a corrugated conduit to maximize vapor removal while minimizing condensate formation and increasing localized residence time in the corrugation. The expiratory tube 117 can include a vapor permeable conduit to maximize vapor removal while minimizing condensation formation. The expiratory tube 117 can include a corrugated, vapor permeable, and/or heated conduit to maximize vapor removal while minimizing condensate formation and increasing localized residence time in the corrugation. Decreased condensate formation within the expiratory tube 117 permits more vapor to diffuse across the wall of the expiratory tube 117. The presence of a heating element 155 can maintain the relative humidity of the gases below 100% (that is, maintain the gases temperature above the dewpoint saturation temperature). Positioning the heating element 155 near or within the wall of the expiratory tube 117 causes the heating element 155 to primarily heat the gases near the wall of the expiratory tube 117. Keeping the gases temperature near the wall of the expiratory tube 117 above dewpoint avoids or limits condensate formation. The inspiratory tube 103 and the expiratory tube 117 are described in even greater detail elsewhere in this specification.

It was realized that incorporating the inspiratory tube 103 with a smaller diameter, smooth bore conduit in conjunction with the expiratory tube 117 with a corrugated conduit allows the expiratory tube 117 to be larger in diameter and/or longer than otherwise would be possible while maintaining the overall system compressible volume. Additionally or alternatively, the combination of the smaller diameter, smooth bore inspiratory tube 103 and the larger diameter, corrugated expiratory tube 117 can maintain the overall pressure drop. Additionally or alternatively, the combination of the smaller diameter, smooth bore inspiratory tube 103 and the larger diameter, corrugated expiratory tube 117 can maintain the resistance to flow (RTF), of the breathing circuit 100 at a desirable level. Ordinarily, increasing the length of a conduit undesirably increases the compressible volume of the conduit, and therefore, the compressible volume of the overall breathing circuit. Ordinarily, increasing the length of a conduit undesirably increases the RTF of the conduit, and therefore, increases the RTF of the overall breathing circuit. On the other hand, when the conduit is vapor permeable, the increased length advantageously improves the conduit's ability to remove vapor from exhaled gases. It was discovered that the combination of the inspiratory tube 103 with a smaller diameter, smooth bore and the expiratory tube 117 with a corrugated, vapor-permeable, larger bore conduit increases the ability of the expiratory tube 117 to remove water vapor from the breathing circuit without increasing the overall system compressible volume, pressure drop, and/or RTF.

It was further realized that incorporating the inspiratory tube 103 with a smooth bore conduit in conjunction with the expiratory tube 117 with a corrugated conduit allows the humidifier 107 to increase humidity performance providing a therapeutic benefit to patients, while driving closer to fully saturated gases, without adding the risk of liquid damage to the gases source 105 or condensate draining back to patient.

The inspiratory tube 103 with a smooth bore, spiral wound conduit can be paired with the expiratory tube 117 with a corrugated, vapor permeable conduit. As discussed above, the smooth bore of the inspiratory tube 103 has lower RTF than a similarly sized corrugated bore. It can also have a smaller internal diameter than a corrugated conduit. Ordinarily, decreasing internal diameter reduces compressible volume and undesirably increases the inspiratory tube's RTF. Nevertheless, the smooth bore characteristics can be selected such that the reduction in RTF associated with the smooth bore of the inspiratory tube 103 outweighs the RTF increase resulting from the smaller internal diameter of the inspiratory tube 103. This selection of a smaller diameter inspiratory tube 103 also reduces the compressible volume of the inspiratory tube 103. This selection then allows the corrugated expiratory tube 117 paired with the smooth bore inspiratory tube 103 to be longer without increasing the overall system pressure drop and/or compressible volume. The increased length of the expiratory tube 117 ordinarily undesirably increases the RTF and compressible volume of the tube. However, the increased length also improves the ability of the vapor permeable tube to remove vapor from expiratory gases. In this arrangement, pairing the smooth bore inspiratory tube 103 with the corrugated expiratory tube 117 enhances the performance of the expiratory tube 117. The system pressure drop of a breathing circuit as may exist from ventilator outlet to ventilator inlet can be affected by the pressure characteristics (RTF) of each element in the circuit. Referring back to FIG. 1A, assuming the pressure characteristics of the supply tube from ventilator to humidifier, humidifier chamber, interface tube, and interface body are fixed, the primary factors contributing to system pressure drop are the resistance to flow and dimensions (length and diameter) of the inspiratory tube 103 and the expiratory tube 117. Any change to one of these factors should advantageously be balanced by other factor(s) to avoid increasing the system pressure drop, RTF and/or compressible volume. As described herein, the primary factors contributing to compressible volume are the tube profile, extensibility, and dimensions (length and diameter or cross-sectional area) of the inspiratory tube 103 and the expiratory tube 117. There can be a tradeoff between decreasing the compressible volume of the inspiratory tube 103 and increasing the compressible volume of the expiratory tube 117 while maintaining the compressible volume of the breathing circuit. As described herein, increasing the compressible volume of the expiratory tube 117 has advantages in in vapor permeability in the expiratory limb.

The smooth bore of the inspiratory tube 103 can reduce resistance to flow (as compared to a corrugated inspiratory tube), decreasing the overall system pressure drop. This allows any or all of the other three factors (resistance to flow of the corrugated expiratory tube 117 or dimensions of either tube) to be altered in a way that increases the system pressure drop. The internal diameter of the inspiratory tube 103 can be smaller than the comparable corrugated inspiratory tube, which desirably increases the velocity of the gases flowing through the inspiratory tube 103. However, the smaller diameter also adds back some resistance to flow. So long as the RTF increase caused by the smaller diameter is sufficiently smaller than the RTF decrease caused by the use of the smooth bore, the length of the corrugated expiratory tube 117 can be increased without increasing the system pressure drop. Increasing the length of the expiratory tube 117 increases the surface area of the tube wall of the expiratory tube 117. The amount of vapor that can be diffused through a vapor permeable material is correlated to the surface area of the material. Increasing the length of the expiratory tube 117 increases the surface area of the wall of the expiratory tube 117 and also increases the residence time of gases in the expiratory tube 117. The amount of vapor that can be diffused through a permeable material is also correlated to the length of time the vapor-carrying gases are in contact with the material.

The compressible volume of the breathing circuit (the cumulative volume of the entire gases flow path) can also be balanced in the same way. For instance, a change in dimensions (cross-sectional area or diameter, length) of the inspiratory tube 103 can offset a change in dimensions (cross-sectional area or diameter, length) of the corrugated expiratory tube 117. As described herein, the decrease in diameter of the inspiratory tube 103 can decrease compressible volume. This decrease in compressible volume can improve accuracy of the delivered tidal volume. As described herein, the decrease in diameter of the inspiratory tube 103 can offset an increased diameter and/or an increased length of the expiratory tube 117. As described herein, the change in dimensions of the expiratory tube 117 can facilitate the function of the expiratory tube 117, such as by increasing vapor permeability of the expiratory tube 117. Altering tube dimensions affects both the system pressure drop and the system compressible volume, so both equations should advantageously be balanced or selected simultaneously when making changes. Reducing the diameter of the inspiratory tube 103 can both increase resistance to flow and decrease compressible volume, while increasing the average gases velocity through the tube. Adding to the length of the corrugated expiratory tube 117 both increases resistance to flow and increases compressible volume. Table 1 (above) summarizes the impacts of various features on these two system metrics:

Pairing the corrugated expiratory tube 117 with the smooth bore inspiratory tube 103 enables higher performance of the inspiratory tube 103. Pairing the larger diameter expiratory tube 117 with the smaller bore inspiratory tube 103 can be net neutral for compressible volume, but increase functionality of the breathing circuit (e.g., increase vapor diffusion in the expiratory tube 117). In this arrangement, the smooth bore inspiratory tube 103 minimizes condensate creation, and therefore maximizes humidity delivery. The overall compressible volume can be decreased by changes in dimensions, such as diameter and length of the inspiratory tube 103 and the expiratory tube 117. In some arrangements, the inspiratory tube 103 is insulated, which helps to make the humidifier 107 and/or a heating element, such as heater plate 131, more efficient in producing humidity that is delivered to the patient 101. The heater plate 131 does not have to work as much because it does not have to produce a high target temperature at the humidification chamber port 111, and this is because the heated and insulated inspiratory tube 103 will better maintain the absolute humidity of the gases flowing from the humidification chamber port 111 and through the inspiratory tube 103.

The location of a heater wire 145 in the wall of the inspiratory tube 103 also increases the efficiency of the inspiratory tube 103 in maintaining the relative humidity of the gas. The heater wire can heat the wall of the inspiratory tube 103, not the gases flowing through the lumen of the inspiratory tube 103, which reduces the relative humidity of the gases near the wall of the inspiratory tube 103. When the inspiratory tube 103 includes a composite conduit with a spiral wound hollow body or "bubble" tube (described in greater detail below), the heater wire 145 is under (on the lumen side of an inner wall) the insulating bubble, which reduces heat loss outward through the wall of the inspiratory tube 103.

The smooth bore inspiratory tube 103 promotes laminar gases flow, which creates a more parabolic wavefront across the lumen of the inspiratory tube 103, with the gases closer to the center of the lumen having a higher velocity relative to gases closer to the wall of the inspiratory tube 103. In this arrangement, the higher velocity gases have less time during transit from the inlet 109 to the outlet 113 to transfer heat to neighboring lower velocity gases. Combined with the inward direction of the heat generated by the heater wire, this arrangement helps to further increase the heat retained by the gases flow.

The smooth bore inspiratory tube 103 also provides no pockets in which vapor could be trapped or condensate might pool, as a corrugated tube would have. The vapor carried by the gases is therefore encouraged to remain in vapor phase and exit the inspiratory tube 103 and thus be delivered to the patient 101.

The corrugated expiratory tube 117 maximizes vapor removal and minimizes condensate formation. The expiratory tube 117 can be vapor permeable which promotes diffusion of vapor through the wall of the expiratory tube 117 to the outside atmosphere. In some arrangements, the expiratory tube 117 is vapor permeable and heated, the control of the heating along the tube promotes diffusion of vapor through the wall of the expiratory tube 117 to the outside atmosphere. Vapor transferred to the outside atmosphere will not be delivered to the gases source 105. The corrugated expiratory tube 117 creates turbulence in the portion of the gases flow adjacent the wall of the expiratory tube 117, which increases the residence time of gases adjacent the wall in the corrugations. Increased residence time increases the opportunity for vapor diffusion through the wall of the expiratory tube 117. Increased residence time also decreases the temperature of the gases swirling in the "pocket" of each corrugation, which increases the relative humidity of those gases. The increased relative humidity increases the vapor pressure gradient across the wall of the expiratory tube 117, which in turn increases vapor diffusion through the wall.

As discussed below, the expiratory tube 117 can include a heater wire 155 coiled near the center of the lumen of the expiratory tube 117. The heater wire, so positioned, adds to the turbulence of the gases flow while minimizing condensate formation. More turbulence means better mixing of the gases, thereby causing the water vapor to travel to the outer walls of the expiratory tube 117. The corrugated expiratory tube 117 also provides corrugation "pockets" that have the advantage of collecting any liquid that condenses from vapor. Liquid pooled in the corrugations is liquid not delivered to the gases source 105. In other arrangements, the heater wire can be positioned in the wall of an expiratory tube. The presence of a heater wire 155 in the expiratory tube 117 also minimizes condensate formation within the expiratory tube.

The combination of the smooth bore inspiratory tube 103 with the corrugated expiratory tube 117 allows the humidifier 107 to increase humidity performance. There is a contribution from the patient and bias flow in both invasive and non-invasive ventilation. In both, the expiratory tube 117 can function to decrease the amount of humidity returned to the gases source 105. The function of the expiratory tube 117 can be to sufficiently reduce the amount of humidity returned to the gases source 105.

The function of the expiratory tube can enable the humidifier 107 and the inspiratory tube 103 to deliver higher levels of humidity to the patient 101. If the expiratory tube 117 could not sufficiently reduce the amount of humidity returned to the gases source 105, the ability of the humidifier 107 and the inspiratory tube 103 to deliver higher levels of humidity to the patient 101 would have to be reduced or dialed back, because some of that extra humidity would be carried through the expiratory tube 117 to the gases source 105.

The inspiratory tube 103 and the expiratory tube 117 are discussed in further detail below.

Inspiratory Tubes

FIG. 2A shows a side plan view of a section of a conduit 201 of an inspiratory tube. In general, the conduit 201 comprises a first elongate member 203 and a second elongate member 205. Member is a broad term and is to be given its ordinary and customary meaning to a person of ordinary skill in the art (i.e., it is not to be limited to a special or customized meaning) and includes, without limitation, integral portions, integral components, and distinct components. The first elongate member 203 has a "bubble" profile, while the second elongate member 205 is a structural supporting or reinforcement member which adds structural support to the hollow body. As used herein, any reference to "bubble" means a an elongate hollow body that, in cross-section, has a shape defined by a wall with a hollow space within. Such shapes could include an oval or "D" shape, with reference to FIG. 2B. Such shapes could include, without limitation, "0" shapes, and other regular and irregular shapes, symmetric and asymmetric. In this description, the term "bubble" can refer to the cross-sectional shape of an elongated wind or turn of the first elongate member 203, taken in transverse cross-section through the wind or turn, for example as shown in FIG. 2B. The hollow body and the structural supporting member can have a spiral configuration, as described herein. The conduit 201 may be used to form the inspiratory tube 103 as described above, a coaxial tube as described below, or any other tubes as described elsewhere in this disclosure.

The first elongate member 203 can comprise a hollow body spirally wound to form, at least in part, an elongate tube having a longitudinal axis LA-LA and a lumen 207 extending along the longitudinal axis LA-LA. A portion 211 of the first elongate member 203 forms at least part of the inner wall of the lumen 207. The first elongate member 203 can be a tube. Preferably, the first elongate member 203 is flexible. Flexible refers to the ability to bend. Furthermore, the first elongate member 203 is preferably transparent or, at least, semi-transparent or semi-opaque. A degree of optical transparency allows a caregiver or user to inspect the lumen 207 for blockage or contaminants or to confirm the presence of moisture (i.e., condensation). A variety of plastics, including medical grade plastics, are suitable for the body of the first elongate member 203. Suitable materials include Polyolefin elastomers, Polyether block amides, Thermoplastic co-polyester elastomers, EPDM-Polypropylene mixtures, and Thermoplastic polyurethanes.

The hollow body structure of the first elongate member 203 contributes to the insulating properties of the conduit 201. An insulating conduit is desirable because, as explained above, it prevents heat loss. This can allow the conduit 201 to deliver gases from the humidifier 107 to the patient 101 while maintaining the conditioned state of the gases with minimal energy consumption.

The second elongate member 205 is also spirally wound and joined to the first elongate member 203 between adjacent turns of the first elongate member 203. The second elongate member 205 forms at least a portion of the lumen 207 of the elongate tube. The second elongate member 205 acts as structural support for the first elongate member 203. The second elongate member 205 can be wider at the base (proximal the lumen 207) and narrower at the top. The second elongate member can be generally triangular in shape, generally T-shaped, or generally Y-shaped. However, any shape that meets the contours of the corresponding first elongate member 203 is suitable.

Preferably, the second elongate member 205 is flexible, to facilitate bending of the tube. Desirably; the second elongate member 205 is less flexible than the first elongate member 203. This improves the ability of the second elongate member 205 to structurally support the first elongate member 203. The second elongate member 205 can be solid or mostly solid.

The second elongate member 205 can encapsulate or house conductive material, such as filaments, and specifically filaments used to generate heat or to carry information from sensors (not shown). Heating elements can comprise filaments, can minimize the cold surfaces onto which condensate from moisture-laden gases can form. Heating elements can also be used to alter the temperature profile of gases in the lumen 207 of the conduit 201. A variety of polymers and plastics, including medical grade plastics, are suitable for the body of the second elongate member 205. Suitable materials include Polyolefin elastomers, Polyether block amides, Thermoplastic co-polyester elastomers, EPDM-Polypropylene mixtures and Thermoplastic polyurethanes. The first elongate member 203 and the second elongate member 205 may be made from the same material.

FIG. 2B shows a longitudinal cross-section of a top portion of the conduit 201 of FIG. 2A. FIG. 2B has the same orientation as FIG. 2A. The first elongate member 203 can have a hollow-body shape. The first elongate member 203 can form in longitudinal cross-section a plurality of hollow bubbles. Portions 209 of the first elongate member 203 overlap adjacent wraps of the second elongate member 205. A portion 211 of the first elongate member 203 forms at least part of the wall of the lumen 207 (tube bore). Adjacent bubbles can be separated by a gap 213. A T-shaped second elongate member 205, as shown in FIG. 2B, can help maintain a gap 213 between adjacent bubbles.

The first elongate member 203 forms in longitudinal cross-section a plurality of hollow bubbles.

One or more conductive materials can be disposed in the second elongate member 205 for heating or sensing the gases flow. Two heating elements 215 can be encapsulated in the second elongate member 205, one on either side of the vertical portion of the "T." The heating element 215 comprise conductive material, such as alloys of Aluminum (Al) and/or Copper (Cu), or conductive polymer. Preferably, the material forming the second elongate member 205 is selected to be non-reactive with the metal in the heating element 215 when the heating elements 215 reach their operating temperature. The heating elements 215 may be spaced away from the lumen 207 so that the elements are not exposed to the lumen 207. At one end of the composite tube, pairs of elements can be formed into a connecting loop. A plurality of filaments can be disposed in the second elongate member 205.

Table 2 shows some non-limiting sample dimensions of two different composite conduits described herein, one for use with infants and the other for use with adults, as well as some non-limiting sample ranges for these dimensions. The dimensions refer to a transverse cross-section of a tube. In these tables, lumen diameter represents the inner diameter of a tube. Pitch represents the distance between two repeating points measured axially along the tube, namely, the distance between the tip of the vertical portions of adjacent "T"s of the second elongate member 205. Bubble width represents the width (maximum outer diameter) of a bubble. Bubble height represents the height of a bubble from the tube lumen. Bead height represents the maximum height of the second elongate member 205 from the tube lumen (e.g., the height of the vertical portion of the "T"). Bead width represents the maximum width of the second elongate member 205 (e.g., the width of the horizontal portion of the "T"). Bubble thickness represents the thickness of the bubble wall.

TABLE 2

| Feature | Infant | | Adult | |
|---|---|---|---|---|
| | Dimension (mm) | Range (±) | Dimension (mm) | Range (±) |
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 2.4 | 1 |
| Bubble height | 2.8 | 1 | 3.5 | 0.5 |
| Bead width | 0.9 | 0.5 | 1.5 | 0.5 |
| Bubble thickness | 0.4 | 0.35 | 0.2 | 0.15 |

Tables 3 and 4 show properties of a composite tube as described herein (labeled "A") having a heating element integrated inside the second elongate member 205. For comparison, properties of a Fisher & Paykel model RT100 disposable corrugated tube (labeled "B") having a heating element helically wound inside the bore of the tube are also presented.

Measurement of resistance to flow (RTF) was carried out according to Annex A of ISO 5367:2000(E). This publication prescribes a normative list of apparatus, procedure steps, and units in which to express the results of testing resistance to flow by measurement of pressure increase at a rated flow through a breathing tube. It includes variances for testing a breathing tube supplied ready for use or a 1 m length breathing tubing supplied to be cut to length, as well as a variance for testing each limb individually of a dual limb circuit that includes a pair of breathing tubes integrally connected to a Y-piece. The result of the test is the difference between the pressure measured in a reservoir with and without the breathing tube attached to the opening of the reservoir.

The results are summarized in Table 3. As seen below, the RTF for the composite tube is lower than the RTF for the comparably sized model RT100 tube.

TABLE 3

| | RTF (cm $H_2O$) | | | |
|---|---|---|---|---|
| Flow rate (L/min) | 3 | 20 | 40 | 60 |
| A | 0 | 0.05 | 0.18 | 0.38 |
| B | 0 | 0.28 | 0.93 | 1.99 |

Condensate or "rainout" within the tube refers to the weight of condensate collected per day at 20 L/min gases flow rate and room temperature of 18° C. Humidified air flows through the tube continuously from a chamber. The tube weights are recorded before and after each day of testing. Three consecutive tests are carried out with the tube being dried in between each test. The results are shown below in Table 4. The results showed that rainout is significantly lower in the composite tube than in the comparably sized model RT100 tube.

TABLE 4

| Tube | A (Day 1) | A (Day 2) | A (Day 3) | B (Day 1) | B (Day 2) | B (day 3) |
|---|---|---|---|---|---|---|
| Weight before (g) | 136.20 | 136.70 | 136.70 | 111.00 | 111.10 | 111.10 |
| Weight after (g) | 139.90 | 140.00 | 139.20 | 190.20 | 178.80 | 167.10 |
| Condensate weight (g) | 3.7 | 3.3 | 2.5 | 79.20 | 67.70 | 56.00 |

A composite tube 201 can comprise one or more heating filaments 215 placed within the gas path. Heating filaments can be emplaced on the lumen wall (tube bore) in a spiral configuration. One or more heating filaments 215 can be disposed on the lumen wall through bonding, embedding, or otherwise forming a heating filament on a surface of the second elongate member 205 that, when assembled, forms the lumen wall. Thus, the method can comprise disposing one or more heating filaments 215 on the lumen wall.

Additional details regarding composite conduits suitable the inspiratory tube 103 are disclosed in the specification and drawings of U.S. patent application Ser. No. 14/123,485, published as U.S. Patent Application Publication No. 2014/0202462 A1 and U.S. patent application Ser. No. 14/649,801, published as U.S. Patent Application Publication No. 2015/0306333 A1, which have been incorporated herein by reference in their entirety for all that they contain.

Expiratory Tubes

As explained above with respect to FIG. 1, breathing circuits can make use of vapor permeable (that is, breathable) expiratory tubes to handle expired gases having high levels of relative humidity. Breathability is desirable to increase vapor diffusion and thus prevent rain out (condensation) in these components. Accordingly, breathing circuits can include vapor permeable expiratory tubes. In general, an expiratory tube comprises an inlet (for receiving expiratory gases), an outlet (for expelling the received gases), and an enclosing wall defining at least one gases passageway between said inlet and said outlet, wherein at least a part of said enclosing wall is of a vapor permeable material allowing the transmission of water vapor but substantially preventing the transmission of liquid water and bulk flow of breathing gases. The expiratory tube can be terminated by a first connector at the inlet and a second connector at the outlet, and only one gases passageway is provided the length between said inlet connector and said outlet connector.

Because of its breathability or vapor permeability, the wall forms a water vapor pathway from the gases space within the tube to the region on the other side of the wall, which may be ambient air. Preferably, the vapor permeable part(s) of the enclosing wall are formed of a foamed material. The tube can comprise an extruded corrugated conduit.

Expiratory tubes including vapor permeable, foamed polymers advantageously have been found to be both breathable and strong. An expiratory tube can comprise a wall defining a space within and wherein at least a part of said wall is of a vapor permeable foamed material, which allows the transmission of water vapor from gases within the space, but prevents the transmission of liquid water. The entire enclosing wall can be formed of the foamed material. Preferably, the wall is also impermeable to bulk flow of gases within the space, including breathing gases. Because of its vapor permeability, the wall forms a water vapor pathway from the gases space to the region on the other side of the wall.

Figure 3A:
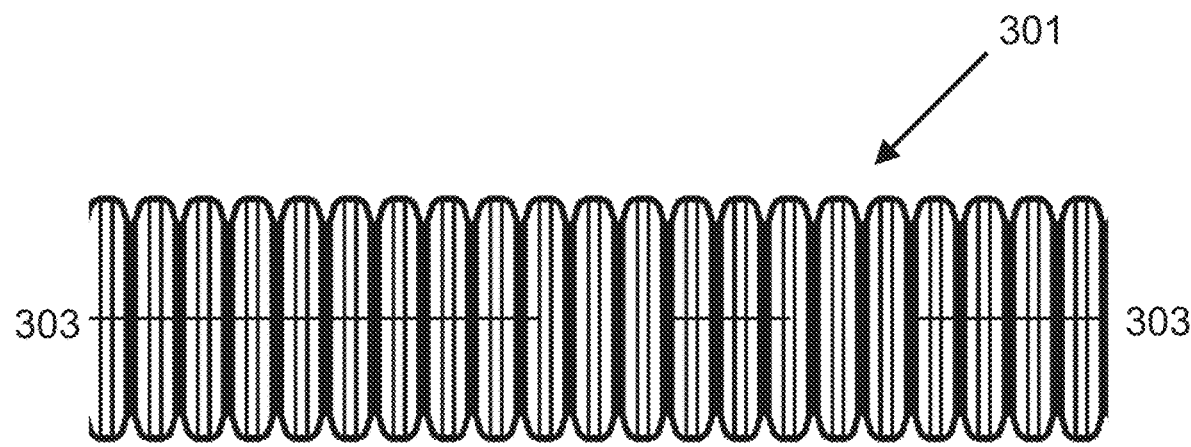
FIG. 3A is a side-plan view of a portion of a tube incorporating a vapor permeable foamed polymer material.
Figure 3B:
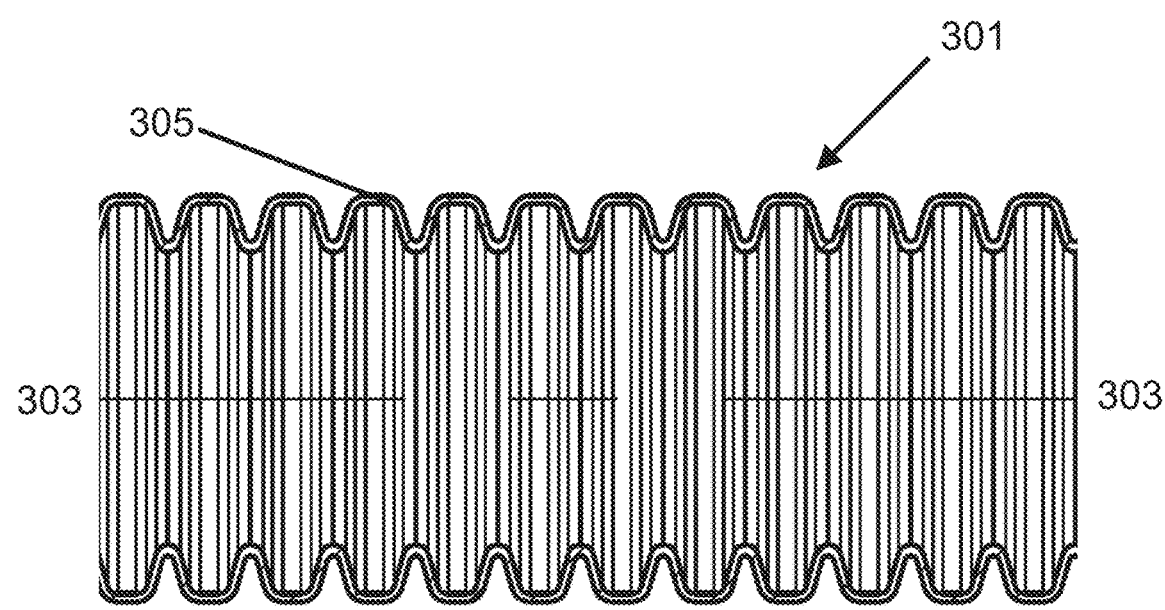
FIG. 3B is cross section view of the tube of FIG. 3A.

Reference is next made to FIGS. 3A and 3B, which show a conduit 301 of an expiratory tube. FIG. 3A shows a side view of the conduit 301, while FIG. 3B shows cross-section of the conduit 301 along the same side view as FIG. 3A. In both FIG. 3A and FIG. 3B, the horizontal axis is indicated as line 303-303. The conduit wall, shown as wall 305 in FIG. 3B is a vapor permeable foamed material. As shown in the figures, the conduit 301 is corrugated. The tube wall, shown as wall 305 in FIG. 3B is a breathable foamed material, as described above.

Because a tube is a type of component, the particulars of the component discussed above are applicable to the tube discussed here. At least a part of the enclosing wall can be comprise a breathable foamed material allowing the transmission of water vapor but substantially preventing the transmission of liquid water and bulk flow of breathing gases. The tube can be an extruded corrugated tube. The medical circuit tube can be used as a breathing tube or conduit or a tube or conduit for a limb of an insufflation system. For instance, the tube can be an expiratory breathing tube or an exhaust conduit, respectively. The tube can also be part of a patient interface. The conduit 301 may be used to form the expiratory tube 117 as described above, a coaxial tube as described below, or any other tubes as described elsewhere in this disclosure.

By incorporating highly breathable or vapor permeable foamed material, components can be manufactured having both a relatively high flexural stiffness and a high breathability. Because of their high vapor permeability (breathability), the foamed polymers allow water vapor to diffuse through them rapidly. This reduces the build-up of condensation within the expiratory tube by transmitting water vapor from the humidified gases within the expiratory tube to the surrounding ambient air or to other drier gases on the other side of the component. Yet, the components formed from these foamed polymers are also stiff, self-supporting, crush resistant, or semi-rigid, have relatively high resistance to crushing and resistance to buckling and even may not require additional reinforcement. The foamed polymers are useful for forming medical circuit components because the foamed polymer allow the transmission of water vapor from gases, but prevent the transmission of liquid water. They are also substantially impermeable to bulk flow of gas, such that they can be used to form components for delivering humidified gases. Foamed polymers can be selected such that the "bulk" properties (thickness, material, material blending, elastic modulus, breathability, and/or bulk stiffness) meet the requirements of the ISO 5367:2000(E) standard (namely, the test for increase in flow resistance) without extra reinforcement, and yet are vapor permeable. ISO 5367:2000(E) is hereby incorporated in its entirety by this reference.

Preferably, the foamed polymer is a vapor permeable foamed thermoplastic polymer. The vapor permeable thermoplastic polymer can be a foamed thermoplastic elastomer (or TPE as defined by ISO 18064:2003(E)), such as (1) a copolyester thermoplastic elastomer (e.g., ARNITEL®, which is a copolyester thermoplastic elastomer with a polyether soft segment, or other TPC or TPC-ET materials as defined by ISO 18064:2003(E)), or (2) a polyether block amide (e.g., PEBAX®, which is a polyamide thermoplastic elastomer with a polyether soft segment, or other TPA-ET materials as defined by ISO 18064:2003(E)), or (3) a thermoplastic polyurethane (TPU material as defined by ISO 18064:2003(E)), or (4) a foamed polymer blend, such as a TPE/polybutylene terephthalate (PBT, e.g., DURANEX® 500FP) blend. It has been found that the vapor permeable TPE ARNITEL® VT 3108 can be particularly suited to foaming and forming components. For this material, the breathability-to-strength relationship can be significantly improved by foaming the material as it is formed into a product or component. If the breathable thermoplastic polymer is a foamed TPE/PBT blend, the blend preferably comprises between 80% and 99% (or about 80% and 99%) TPE by weight and 20% and 1% (or about 20% and 1%) PBT by weight. The void fraction of the foamed material can be greater than 25% (or about 25%), such as between 25 and 60% (or about 25 and 60%), or between 30 and 50% (or about 30 and 50%). The foamed material can be structured such that no more than 5% (or about 5%) of the voids of the foamed material exceed a diameter of 500 μm.

It was discovered that the combined permeability and modulus for all the previously known materials did not exceed line 201, representing the formula: $\ln(P)=0.019 (\ln(M))^2 - 0.7 \ln(M) + 6.5$ in which P represents permeability of the material in g mm/m²/day, measured according to ASTM E96 Procedure A (desiccant method at a temperature of 23° C. and a relative humidity of 90%), and M represents the Young's modulus of the material in MPa.

The breathing circuit can comprise an expiratory tube comprising corrugated and/or vapor permeable materials that are not foam based. In some non-limiting arrangements, the inner wall of the expiratory tube can comprise a helically-wrapped vapor permeable tape. In some arrangements, the inner wall of the expiratory tube comprises a series of beads of varying diameters. Beads of different diameters can be arranged along the inner wall of the expiratory tube to create a corrugated pattern.

The wall can also include at least one reinforcing rib stiffening the wall or at least one region where the wall is locally thickened to stiffen the wall. The tube can include a plurality of reinforcing ribs arranged about the enclosing wall. These ribs can be co-extruded with the tube to be generally aligned with the longitudinal axis of the tube. Preferably, there are three to eight reinforcing ribs, and more particularly, three to five reinforcing ribs.

Figure 4A:
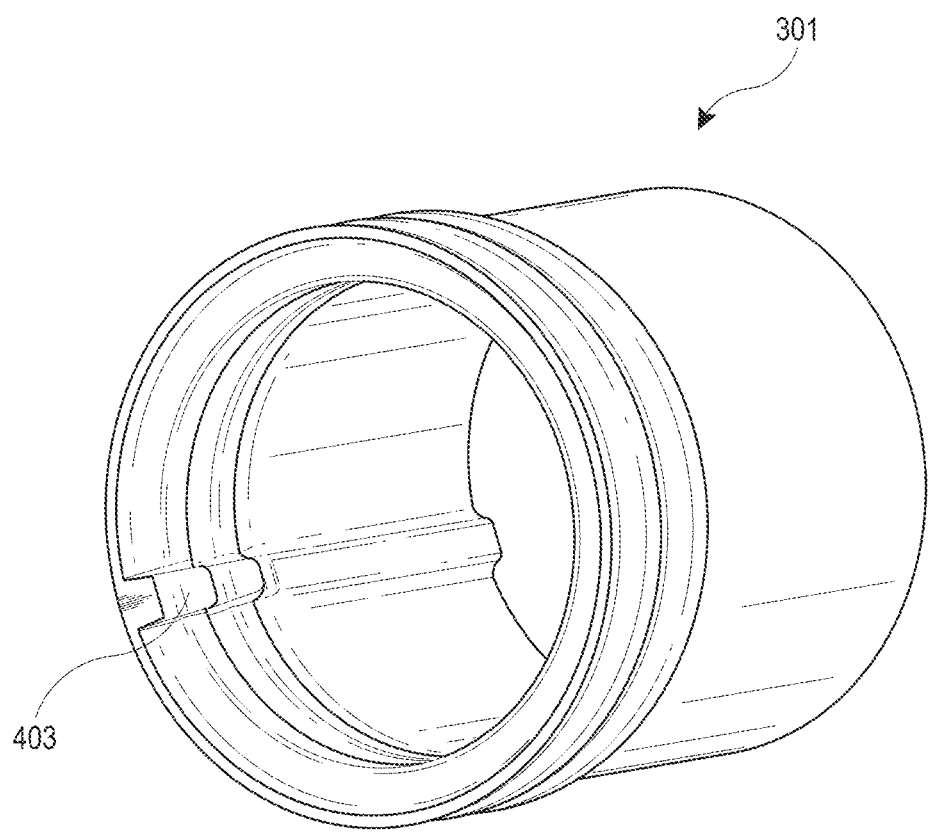
FIG. 4A is a front-perspective view of a portion of a tube incorporating integral, reinforcing ribs, wherein the tube is partially corrugated.
Figure 4B:
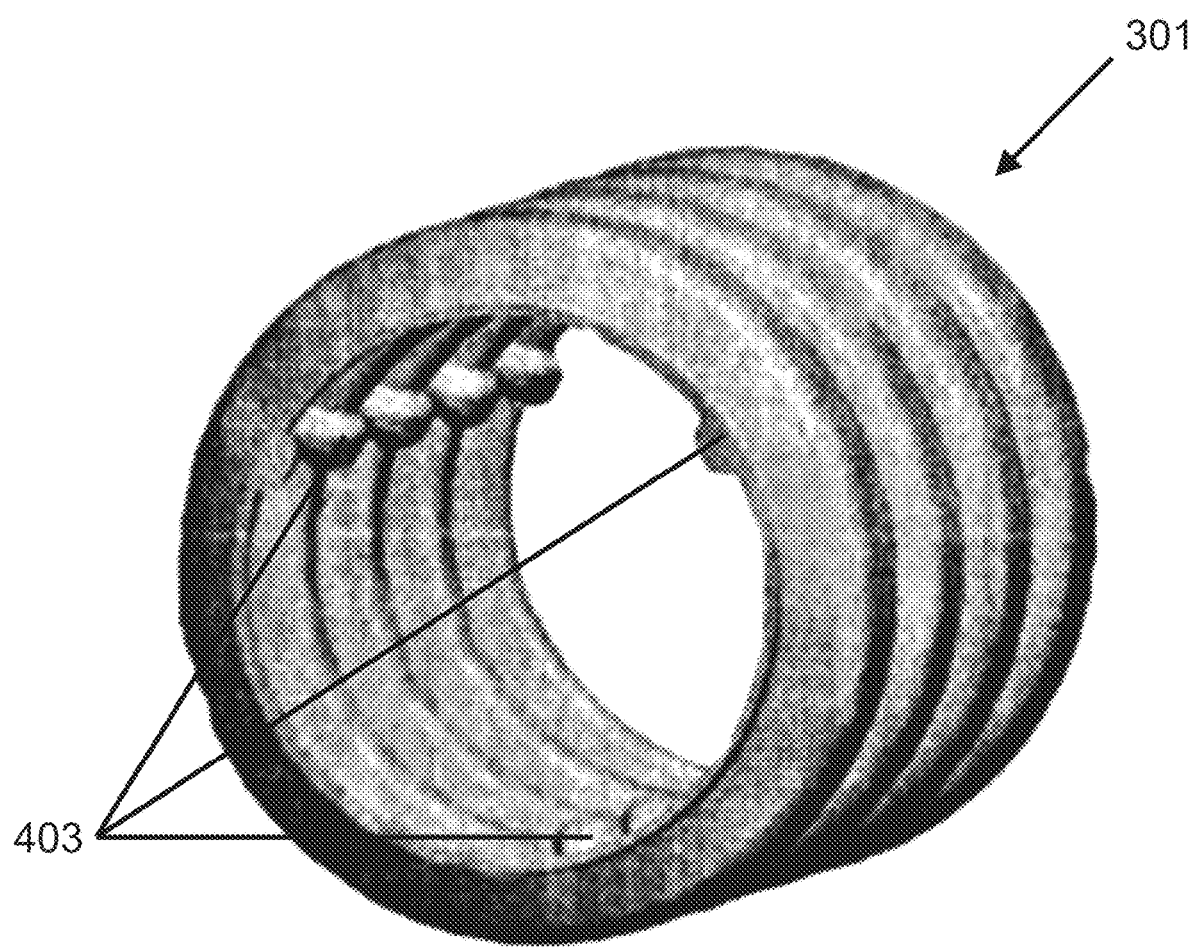
FIG. 4B is a front perspective view of a portion of the tube of FIG. 4A, wherein the tube is fully corrugated.

Reference is next made to FIGS. 4A and 4B, which show a portion of the conduit 301 that can be used to form the expiratory tube 117. The conduit 301 can be manufactured from a foamed vapor permeable material, as described herein. The conduit 301 further includes a plurality of reinforcing ribs 403 that can be co-extruded with the conduit 301. The ribs 403 can be formed from the same foamed polymer as the conduit 301. Alternatively, the ribs 403 can be made from a different material than the conduit 301. This can be achieved by co-extrusion. As shown in FIG. 4A, the conduit 301 can be extruded with the ribs 403 in place, and then corrugated to form the "dotted" structure shown in FIG. 4B. The conduit 301 can comprise between three and eight reinforcing ribs, such as between three and five reinforcing ribs In particular, the ribs can be arranged about the circumference of the tube shape. The ribs can be circumferentially arranged about the inner surface of the tube shape. The ribs can be generally longitudinally aligned along a length of the tube shape between the inlet and the outlet.

Figure 5A:
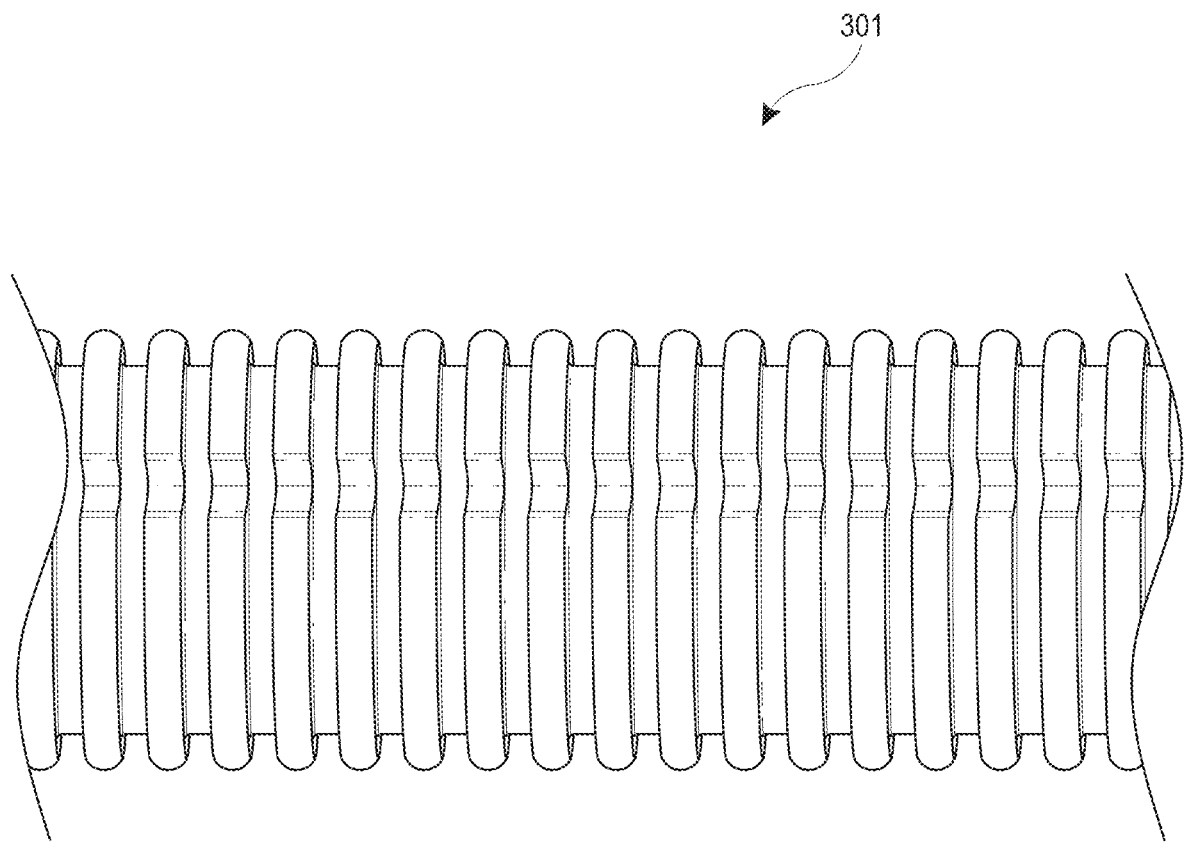
FIG. 5A is a front-perspective view of a portion of a tube incorporating ribs.
Figure 5B:
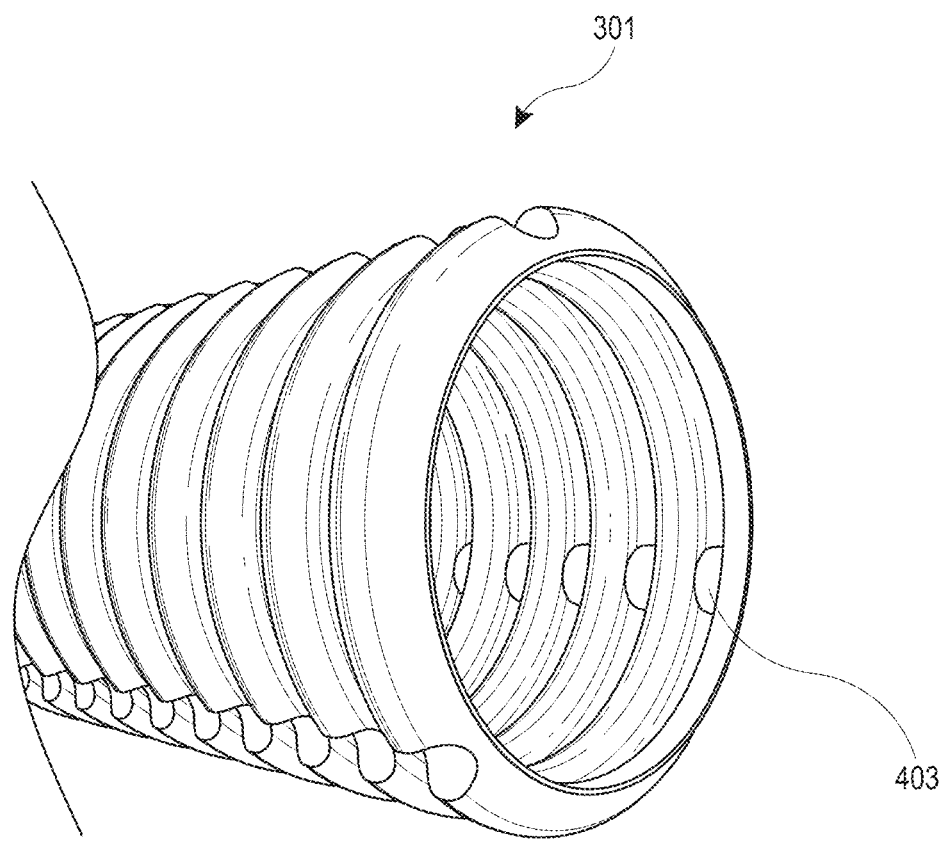
FIG. 5B is a front-perspective view of the tube of FIG. 5A.

Reference is next made to FIGS. 5A and 5B, which show a configuration for the corrugated, ribbed, vapor permeable conduit 301. In FIG. 5 the raised ribs 403 are visible in the space between the ridges in the inside of the conduit 301.

Figure 6:
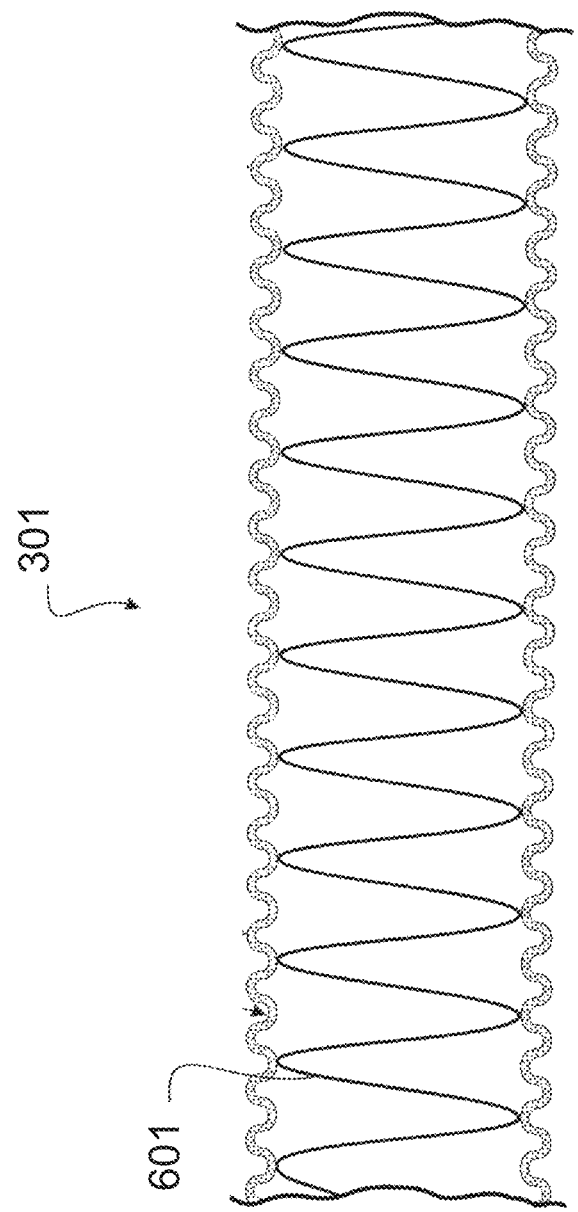
FIG. 6 is a schematic illustration of a portion of an expiratory tube.
Figure 7:
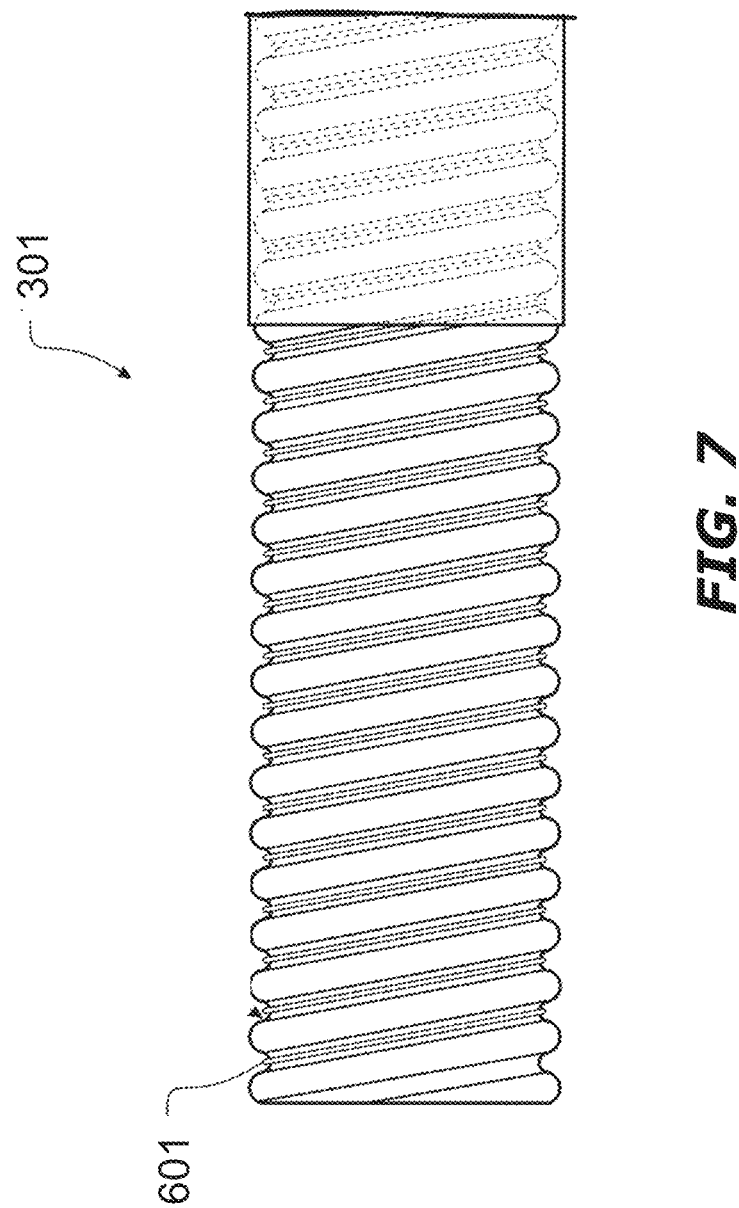
FIG. 7 is a schematic illustration of a portion of an expiratory tube.
Figure 8:
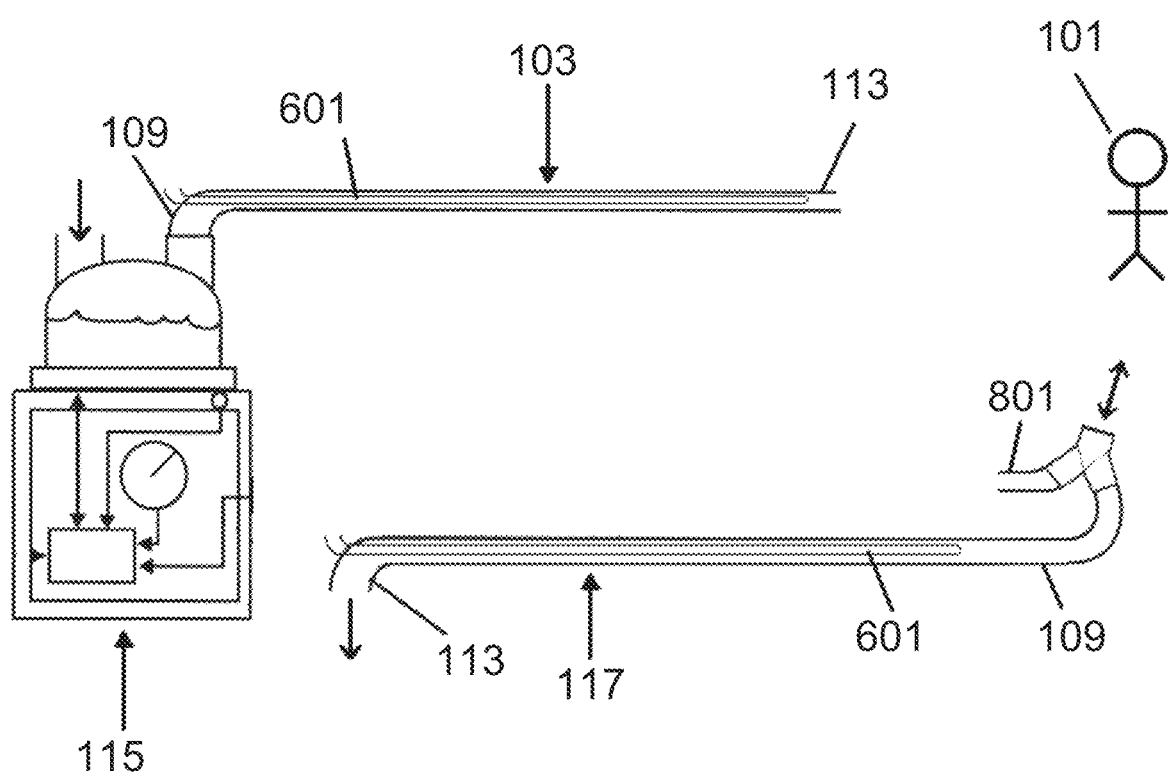
FIG. 8 is a schematic illustration of a breathing circuit including a humidifier, an inspiratory tube, and an expiratory tube.

In addition to the above, to reduce or eliminate the formation of condensation within the tube, a heater, such as a resistance heater wire, may be provided within the conduit 301 passageway, within the conduit 301 wall, or about the external surface of the outer wall surface of the conduit 301. FIG. 6 is a generalized view of the corrugated, foamed-polymer conduit 301 incorporating a heater wire 601 within the passageway of the conduit 301. FIG. 7 is a generalized view of the corrugated, foamed-polymer conduit 301 incorporating the heater wire 601 about the external surface of the outer wall surface of the conduit 301. FIG. 8 includes a schematic view of the expiratory tube 117 incorporating the heater wire 601 within the tube wall.

Additional details regarding expiratory tubes are disclosed in the specification and drawings of U.S. patent application Ser. No. 13/517,925, published as U.S. Patent Application Publication No. 2013/0098360 A1, which has been incorporated herein by reference in its entirety for all that it contains.

Reference is further made to FIG. 8, which shows a breathing circuit that comprises the inspiratory tube 103 and the expiratory tube 117. The properties of the inspiratory tube 103 and the expiratory tube 117 are similar to those described above with respect to FIG. 1 through FIG. 7. The inspiratory tube 103 has the inlet 109, communicating with the humidifier 107, and the outlet 113, through which humidified gases are provided to the patient 101. The expiratory tube 117 also has an inlet 109, which receives exhaled gases from the patient 101, and an outlet 113. As described above with respect to FIG. 1, the outlet 113 of the expiratory tube 117 can vent exhaled gases to the atmosphere, to the gases source 105, to an air scrubber/filter (not shown), or to any other suitable location.

As described above with respect to FIGS. 1, 6, and 7, the heating wires 215 can be included in the inspiratory tube 103 and/or the heating wire 601 can be included in the expiratory tube 117 to reduce the risk of condensate formation in the tubes by raising the temperature of the gases (primarily the gases near the tube wall) above the saturation temperature. It should be understood that the heating wires can desirably include coiled or helical configurations and are shown as straight lines for conceptual purposes. The breathing circuit can comprise a connector (a Y-connector or wye-piece 801) for connecting the inspiratory tube 103 and the expiratory tube 117 to a patient interface (not shown). Of course, it should be understood that other breathing circuit configurations are within the scope of the disclosure.

The foregoing description includes preferred forms of the invention. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

What is claimed is:

1. A respiratory circuit comprising a combination of a smooth bore inspiratory tube to deliver humidified gases to a patient and a corrugated expiratory tube to increase removal of vapor from expiratory gases, the respiratory circuit comprising:
   the smooth bore inspiratory tube for carrying inspiratory gases to the patient, the smooth bore inspiratory tube comprising a first elongate member, the first elongate member comprising a hollow body spirally wound to form at least in part an inspiratory central bore and a wall surrounding the inspiratory central bore, wherein the inspiratory central bore is smooth, and a second elongate member spirally wound and joined between adjacent turns of the first elongate member, the second elongate member forming at least in part the inspiratory central bore, the smooth bore inspiratory tube comprising a smaller internal diameter than a comparable corrugated tube having a similar resistance to flow, the smaller internal diameter decreasing a compressible volume of the smooth bore inspiratory tube relative to the comparable corrugated tube;
   the corrugated expiratory tube for carrying expiratory gases from the patient, the corrugated expiratory tube comprising an inlet and an outlet, the corrugated expiratory tube comprising a wall, the wall enclosing an expiratory central bore, wherein the wall is configured to contain the expiratory gases and is permeable to water vapor and substantially impermeable to liquid water and bulk flow of the expiratory gases, wherein the expiratory central bore is corrugated; and
   a connector that in use connects the outlet of the smooth bore inspiratory tube and the inlet of the corrugated expiratory tube to the patient to transfer the inspiratory gases to the patient and the expiratory gases from the patient.

2. The respiratory circuit of claim 1, wherein the wall of the third elongate member comprises a foamed polymer that is permeable to water vapor and substantially impermeable to liquid water and bulk flow of the expiratory gases.

3. The respiratory circuit of claim 2, wherein the foamed polymer comprises a solid thermoplastic elastomer material having cell voids distributed throughout.

4. The respiratory circuit of claim 1, wherein the second elongate member of the smooth bore inspiratory tube encloses at least one heating element.

5. The respiratory circuit of claim 1, wherein the first elongate member of the smooth bore inspiratory tube forms in longitudinal cross-section a plurality of bubbles each with a flattened surface forming at least part of the wall surrounding the inspiratory central bore.

6. The respiratory circuit of claim 5, wherein the second elongate member of the smooth bore inspiratory tube encloses at least one heating element.

7. The respiratory circuit of claim 6, wherein the at least one heating element is between at least one of the plurality of bubbles and the inspiratory central bore of the smooth bore inspiratory tube.

8. The respiratory circuit of claim 1, wherein the second elongate member of the smooth bore inspiratory tube encloses a heating element.

9. The respiratory circuit of claim 1, wherein the wall of the corrugated expiratory tube encloses a heating element within the expiratory central bore, or
   wherein the corrugated expiratory tube comprises a heating element attached to the wall enclosing the expiratory central bore, or wherein the corrugated expiratory tube comprises a heating element embedded in the wall enclosing the expiratory central bore.

10. The respiratory circuit of claim 1, wherein the wall enclosing the expiratory central bore has an inner surface adjacent to the expiratory central bore and the corrugated expiratory tube further comprises a plurality of reinforcing ribs circumferentially arranged around the inner surface and generally longitudinally aligned between the inlet and the outlet.

11. A device comprising:
   a respiratory circuit comprising:
   a smooth bore inspiratory tube configured to receive an inspiratory gases flow from a gas source, the smooth bore inspiratory tube comprising an inspiratory inlet, an inspiratory outlet, and a wall enclosing an inspiratory central bore, wherein the inspiratory central bore is smooth, the smooth bore inspiratory tube comprising a smaller internal diameter than a comparable corrugated tube having a similar resistance to flow, the smaller internal diameter decreasing a compressible volume of the smooth bore inspiratory tube relative to the comparable corrugated tube;
   a corrugated expiratory tube configured to receive an expiratory gases flow from a patient, the corrugated expiratory tube comprising an expiratory inlet, an expiratory outlet, and a wall enclosing an expiratory central bore, wherein the expiratory central bore is corrugated, and wherein the wall of the corrugated expiratory tube is permeable to water vapor and substantially impermeable to liquid water and bulk flow of the expiratory gases flow flowing therethrough; and
   a connector configured to connect in use the smooth bore inspiratory tube and the corrugated expiratory tube to the patient to transfer the inspiratory gases flow to the patient and the expiratory gases flow from the patient.

12. The device of claim 11, wherein the smooth bore inspiratory tube comprises a first elongate member comprising a hollow body spirally wound to form at least in part the inspiratory central bore and the wall enclosing the inspiratory central bore.

13. The device of claim 12, wherein the smooth bore inspiratory tube comprises a second elongate member spirally wound and joined between adjacent turns of the first elongate member, the second elongate member forming at least in part the inspiratory central bore.

14. The device of claim 11, wherein the wall of the corrugated expiratory tube comprises a foamed polymer that is permeable to water vapor and substantially impermeable to liquid water and bulk flow of the expiratory gases flow.

15. The device of claim 14, wherein the foamed polymer comprises a solid thermoplastic elastomer material having cell voids distributed throughout.

16. The device of claim 11, wherein the smooth bore inspiratory tube encloses a heating element within the inspiratory central bore, or wherein the smooth bore inspiratory tube comprises a heating element attached to the wall of the smooth bore inspiratory tube, or wherein the smooth bore inspiratory tube comprises a heating element embedded in the wall of the smooth bore inspiratory tube.

17. The device of claim 11, wherein the corrugated expiratory tube comprises a heating element within the expiratory central bore, or wherein the corrugated expiratory tube comprises a heating element attached to the wall of the corrugated expiratory tube, or wherein the corrugated expiratory tube comprises a heating element embedded within the wall of the corrugated expiratory tube.

18. The device of claim 11, wherein the smooth bore inspiratory tube comprises in longitudinal cross-section a plurality of bubbles each with a flattened surface forming at least part of the wall of the inspiratory central bore.

19. The device of claim 18, wherein the smooth bore inspiratory tube comprises at least one heating element.

20. The device of claim 19, wherein the at least one heating element is between a bubble of the plurality of bubbles and the inspiratory central bore.

21. The device of claim 11, wherein the corrugated expiratory tube comprises a plurality of reinforcing ribs circumferentially arranged around the wall and generally longitudinally aligned between the expiratory inlet and the expiratory outlet.

22. The device of claim 11, further comprising a humidifier configured to humidify the inspiratory gases flow to the patient, wherein the humidifier comprises:
   a humidification chamber configured to store a volume of liquid and configured to be in fluid communication with the inspiratory gases flow, and
   a heater configured to heat the volume of liquid in the humidification chamber to create vapor, such that the inspiratory gases flow is humidified by the vapor.

23. A respiratory apparatus comprising:
   a humidification chamber configured to be in fluid communication with an inspiratory gases flow;
   a smooth bore inspiratory tube configured to receive the inspiratory gases flow from the humidification chamber, the smooth bore inspiratory tube comprising an inspiratory inlet, an inspiratory outlet, and a wall enclosing an inspiratory central bore, wherein the inspiratory central bore is smooth, the smooth bore inspiratory tube comprising a smaller internal diameter than a comparable corrugated tube having a similar resistance to flow, the smaller internal diameter decreasing a compressible volume of the smooth bore inspiratory tube relative to the comparable corrugated tube;
   a corrugated expiratory tube configured to receive an expiratory gases flow from a patient, the corrugated expiratory tube comprising an expiratory inlet, an expiratory outlet, and a wall enclosing an expiratory central bore, wherein the expiratory central bore is corrugated, and wherein the wall of the corrugated expiratory tube is permeable to water vapor and substantially impermeable to liquid water and bulk flow of the expiratory gases flow flowing therethrough; and
   a connector configured to connect in use the smooth bore inspiratory tube and the corrugated expiratory tube to the patient to transfer the inspiratory gases flow to the patient and the expiratory gases flow from the patient.

* * * * *

UNITED STATES PATENT AND TRADEMARK OFFICE
CERTIFICATE OF CORRECTION

| | |
|---|---|
| PATENT NO. | : 12,053,586 B2 |
| APPLICATION NO. | : 16/317920 |
| DATED | : August 6, 2024 |
| INVENTOR(S) | : James William Stanton et al. |

It is certified that error appears in the above-identified patent and that said Letters Patent is hereby corrected as shown below:

On the Title Page

On Page 2, Column 1, Line 42, item (56) under U.S. Patent Documents, delete "Jeppesen" and insert --Jeppesen et al.--.

In the Claims

In Column 36, Claim 2, Lines 1-2, after "wall" delete "of the third elongate member".

Signed and Sealed this
Twenty-second Day of October, 2024

Katherine Kelly Vidal
*Director of the United States Patent and Trademark Office*